United States Patent
Millward et al.

(10) Patent No.: US 9,034,928 B2
(45) Date of Patent: May 19, 2015

(54) METHODS FOR METABOLIC IMAGING

(71) Applicants: Niki Zacharias Millward, Bellaire, TX (US); Pratip Bhattacharya, Houston, TX (US)

(72) Inventors: Niki Zacharias Millward, Bellaire, TX (US); Pratip Bhattacharya, Houston, TX (US)

(73) Assignee: IMAGNX, Inc., San Francisco, CA (US)

( * ) Notice: Subject to any disclaimer, the term of this patent is extended or adjusted under 35 U.S.C. 154(b) by 0 days.

(21) Appl. No.: 14/157,519

(22) Filed: Jan. 17, 2014

(65) Prior Publication Data

US 2014/0134108 A1 May 15, 2014

Related U.S. Application Data

(63) Continuation of application No. 13/539,456, filed on Jul. 1, 2012, now Pat. No. 8,664,279.

(60) Provisional application No. 61/504,152, filed on Jul. 1, 2011, provisional application No. 61/557,879, filed on Nov. 9, 2011.

(51) Int. Cl.
| | |
|---|---|
| *C07C 69/347* | (2006.01) |
| *A61K 49/10* | (2006.01) |
| *C07C 69/40* | (2006.01) |
| *C07C 69/60* | (2006.01) |
| *G01R 33/46* | (2006.01) |
| *G01R 33/56* | (2006.01) |

(52) U.S. Cl.
CPC ............... *A61K 49/10* (2013.01); *C07C 69/40* (2013.01); *C07C 69/60* (2013.01); *G01R 33/46* (2013.01); *G01R 33/5601* (2013.01)

(58) Field of Classification Search
CPC ....................................................... C07C 69/347
USPC .............................................. 560/1; 514/724
See application file for complete search history.

(56) References Cited

U.S. PATENT DOCUMENTS

| | | | |
|---|---|---|---|
| 6,574,496 B1 | 6/2003 | Golman et al. | |
| 7,022,310 B2 * | 4/2006 | Kainosho et al. | 424/9.34 |
| 2006/0173283 A1 | 8/2006 | Axelsson et al. | |
| 2010/0310467 A1 | 12/2010 | Gisselsson et al. | |

OTHER PUBLICATIONS

Chekmenev, et al., "Hyperpolarized 1H NMR Employing Low [gamma] Nucleus for Spin Polarization Storage," J. Am. Chem. Soc., 2009, 131(9), 3164-3165.
Zacharias, et al., "Real-Time Molecular Imaging of Tricarboxylic Acid Cycle Metabolism in Vivo by Hyperpolarized 1-13C Diethyl Succinate," J. Am. Chem. Soc., 2012, 134, 934-943.
International Search Report issued Sep. 25, 2012 in corresponding PCT Application Ser. No. PCT/US2012/045171.
Hoevener, et al. "PASADENA hyperpolarization of 13C biomolecules: equipment design and installation." MAGMA, 2009, 22(2), 111-121.
Hoevener, et al. "Quality assurance of PASADENA hyperpolarization for 13C biomolecules." MAGMA, 2009, 22(2), 123-134.

\* cited by examiner

*Primary Examiner* — Kamal Saeed
*Assistant Examiner* — Janet L Coppins
(74) *Attorney, Agent, or Firm* — Benesch, Friedlander, Coplan, & Aronoff, LLC; Benjamen E. Kern; Kraig K. Anderson

(57) ABSTRACT

The present embodiments disclose the preparation of hyperpolarized $^{13}C$ dialkyl succinate compounds and hyperpolarized $^{13}C$ dialkyl fumarate compounds and their use in real time, in vivo metabolic imaging of the TCA cycle.

28 Claims, 19 Drawing Sheets

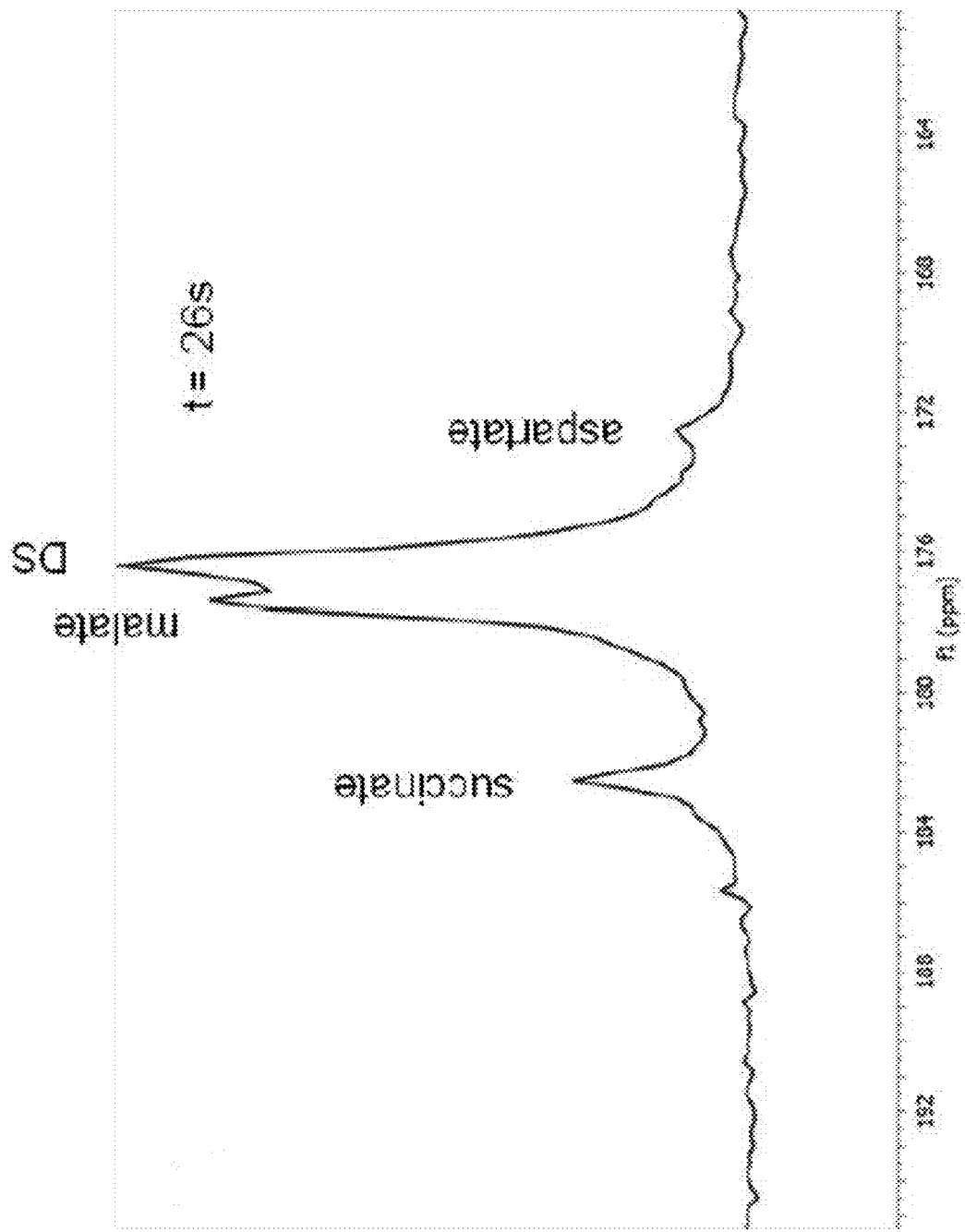

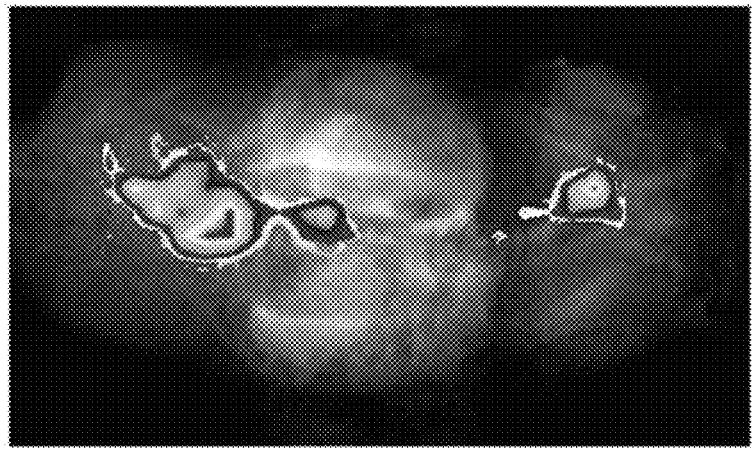
Figure 5B t=37s
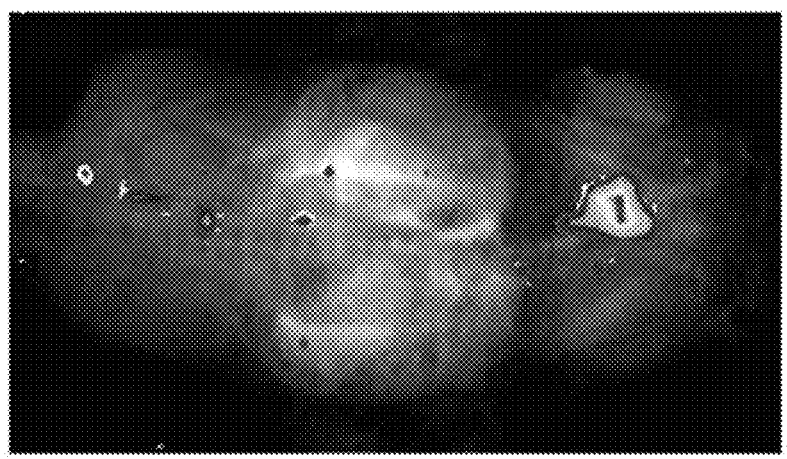
Figure 5A t=34s t=9s t=9s

METHODS FOR METABOLIC IMAGING

CROSS-REFERENCE TO RELATED APPLICATIONS

This application is a continuation of U.S. patent application Ser. No. 13/539,456, filed Jul. 1, 2012, which in turn claims priority to U.S. Provisional Patent Application No. 61/504,152, filed on Jul. 1, 2011, and to U.S. Provisional Patent Application No. 61/557,879, filed on Nov. 9, 2011, each of which are incorporated by reference herein in their entireties.

STATEMENT REGARDING FEDERALLY SPONSORED RESEARCH OR DEVELOPMENT

This invention was made with government support under NIH Grant Nos. 1R21CA118509 and 1R01NS048589, and NCI Grant No. 5R01CA122513. The U.S. Government has certain rights in this invention.

BACKGROUND

The Krebs tricarboxylic acid cycle (the "TCA cycle") and oxidative phosphorylation are central to metabolic energy production. The TCA cycle occurs in the mitochondria of cells and, in most cells, produces the majority of adenosine triphosphate (>90%). In normal cells, the main energy source for the TCA cycle is pyruvate generated from glycolysis of glucose.

Many disease states have perturbed TCA cycles. In cancer, succinate dehydrogenase and fumarate hydratase oncogenes impair the TCA cycle. The TCA cycle can have different entry points. A broad range of energy substrates can be used in the TCA cycle (e.g., citrate and glutamate/glutamine), especially in cancer. Evidence exists that the TCA cycle is altered in many neurodegenerative diseases (e.g., Alzheimer's, Parkinson's, Huntington's, and amyotrophic lateral sclerosis) as well. In addition, adenosine triphosphate ("ATP") is the main energy source for the heart for contraction, maintenance of active ion gradients, and other vital functions. Most of the ATP production of the heart occurs as a result of, and is controlled by, the TCA cycle, and the TCA cycle is altered in many disease states of the heart.

Many of the metabolic differences between disease and normal tissue can and could be examined through the use of metabolic imaging agents. Presently, metabolic imaging is performed with positron emission tomography ("PET") measurements of the uptake of 2-[$^{18}$F]fluoro-2-deoxy-D-glucose ("FDG-glucose") or magnetic resonance spectroscopy ("MRS"). However, PET imaging with FDG-glucose only measures the level of uptake of glucose and phosphorylation, and reveals nothing about the subsequent metabolism of glucose. In MRS, only the steady state of a tissue/organ's metabolic profile can be determined, and, under normal circumstances, MRS's low signal to noise ratio requires lengthy exam times.

More recently, hyperpolarization of molecules has opened the way to real-time metabolic imaging in vivo, i.e., in living human or non-human animal beings. Hyperpolarization allows for over 10,000 fold sensitivity enhancement using conventional magnetic resonance imaging ("MRI") and MRS. Upon enhancing the nuclear polarization of nuclear magnetic resonance ("NMR") active nuclei (e.g., $^{13}$C, $^{15}$N, $^{31}$P), the population difference between excited and ground nuclear spin states of the nuclei is increased and the magnetic resonance signal intensity is amplified. The polarization (signal enhancement) may be retained on the metabolites of the hyperpolarized molecule. In addition, unlike PET, the hyperpolarization process is non-radioactive.

The most widely used methods for hyperpolarization are dynamic nuclear polarization ("DNP") and parahydrogen induced polarization ("PHIP"). Several compounds have been hyperpolarized and studied using hyperpolarized metabolic imaging. For example, 1-$^{13}$C pyruvate, 1,4-$^{13}$C fumarate, $^{13}$C succinate, $^{13}$C 2-hydroxy ethyl propionate, and 2,2,3,3-tetrafluoropropyl-1-$^{13}$C priopionate-d$_{2,2,3,3}$ ("TFPP") have been studied in in vivo applications. However, all of these compounds have physiological barriers to being used in clinical practice. For example, 1-$^{13}$C pyruvate can be used to follow the metabolism of pyruvate to alanine, lactate, and bicarbonate, but reveals nothing about TCA cycle metabolism. For $^{13}$C succinate, the polarization transfer must be performed under acidic (pH≤3) or alkaline (pH≥9) conditions for optimum hyperpolarization. In addition, $^{13}$C succinate is only poorly transported across many biological membranes and, in particular, barely crosses the mitochondrial membrane to gain access to TCA cycle enzymes involved in metabolism. $^{13}$C 2-hydroxy ethyl propionate is toxic and is not metabolized. TFPP is not very water soluble and has to be injected in a 20% ethanol aqueous solution.

Hyperpolarized compounds are needed that: (1) are metabolized by the TCA cycle; and (2) are capable of use as diagnostic in vivo imaging agents.

SUMMARY

In one embodiment, a composition comprising a hyperpolarized dialkyl $^{13}$C succinate compound having Formula I is provided:

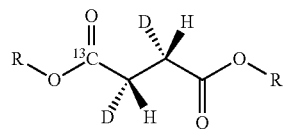

wherein R may be selected from methyl, ethyl, n-propyl, i-propyl, n-butyl, i-butyl, or t-butyl.

In another embodiment, a composition is provided, the composition comprising hyperpolarized diethyl 1-$^{13}$C succinate and diethyl 1,4-$^{13}$C succinate.

In one embodiment, a method for metabolic imaging of a patient is provided, the metabolic imaging comprising:
administering to the patient a diagnostically effective amount of a composition comprising hyperpolarized dialkyl $^{13}$C succinate; and
detecting hyperpolarized metabolic products in the patient.

In another embodiment, a composition comprising a hyperpolarized dialkyl $^{13}$C fumarate compound having Formula II is provided:

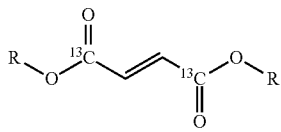

wherein R may be selected from methyl, ethyl, n-propyl, i-propyl, n-butyl, i-butyl, or t-butyl.

In one embodiment, a composition is provided, the composition comprising hyperpolarized diethyl 1,4-$^{13}$C fumarate.

In one embodiment, a method for metabolic imaging of a patient is provided, the metabolic imaging comprising:
administering to the patient a diagnostically effective amount of a composition comprising hyperpolarized dialkyl $^{13}$C fumarate; and
detecting hyperpolarized metabolic products in the patient.

BRIEF DESCRIPTION OF THE DRAWINGS

In the accompanying figures, chemical formulas, chemical structures, and experimental data are given that, together with the detailed description provided below, describe example embodiments of the claimed invention.

FIG. 2B illustrates an enlarged view of a region of interest of the $^{13}$C MRS acquired at t=26 s as seen in the stackplot of FIG. 2A.

FIG. 5A illustrates example overlays of $^{13}$C FISP images (60° flip angle) taken of a mouse after intravenous injection of 10 μmol of hyperpolarized diethyl 1-$^{13}$C 2,3-d$_2$ succinate.

FIG. 5B illustrates example overlays of $^{13}$C FISP images (60° flip angle) taken of a mouse after intravenous injection of 10 μmol of hyperpolarized diethyl 1-$^{13}$C 2,3-d$_2$ succinate.

DETAILED DESCRIPTION

Figure 1A:
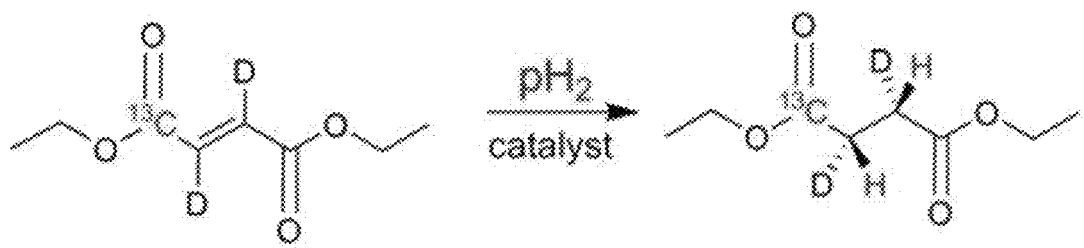
FIG. 1A illustrates an example schematic for the hydrogenation of diethyl 1-$^{13}$C 2,3-d$_2$ fumarate to diethyl 1-$^{13}$C 2,3-d$_2$ succinate with parahydrogen (pH$_2$) using a rhodium bisphosphine catalyst.

The present embodiments disclose the preparation of hyperpolarized dialkyl $^{13}$C succinate and hyperpolarized dialkyl $^{13}$C fumarate compounds and their use in real time, in vivo metabolic imaging of the TCA cycle.

In one embodiment, a composition comprising a hyperpolarized dialkyl $^{13}$C succinate compound having Formula I is provided:

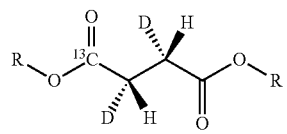

I wherein R may be selected from methyl, ethyl, n-propyl, i-propyl, n-butyl, i-butyl, or t-butyl. In one embodiment, R=methyl. In one embodiment, R=ethyl. In one embodiment, R=n-propyl. In one embodiment, R=i-propyl. In one embodiment, R=n-butyl. In one embodiment, R=i-butyl. In one embodiment, R=t-butyl. In another embodiment, a composition is provided, the composition comprising hyperpolarized diethyl $^{13}$C succinate. In a particular embodiment, the hyperpolarized diethyl $^{13}$C succinate comprises hyperpolarized diethyl 1-$^{13}$C 2,3-d$_2$ succinate. Diethyl succinate is a neutral molecule, can be used at physiological pH, and crosses biological membranes. Diethyl succinate can be incorporated into cells in tissue culture, and is metabolized in the TCA cycle. In addition, diethyl succinate is non-toxic.

In one embodiment, hyperpolarized dialkyl $^{13}$C succinate is useful for metabolic imaging of a patient. In one embodiment, a method for metabolic imaging of a patient using hyperpolarized dialkyl $^{13}$C succinate is provided, the metabolic imaging comprising: administering to the patient a diagnostically effective amount of a composition comprising hyperpolarized dialkyl $^{13}$C succinate; and detecting hyperpolarized metabolic products in the patient.

In another embodiment, a composition comprising a hyperpolarized dialkyl $^{13}$C fumarate compound having Formula II is provided:

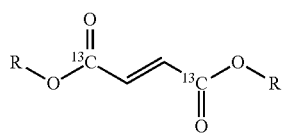

II wherein R may be selected from methyl, ethyl, n-propyl, i-propyl, n-butyl, i-butyl, or t-butyl. In one embodiment, R=methyl. In one embodiment, R=ethyl. In one embodiment, R=n-propyl. In one embodiment, R=i-propyl. In one embodiment, R=n-butyl. In one embodiment, R=i-butyl. In one embodiment, R=t-butyl.

In another embodiment, a composition is provided, the composition comprising hyperpolarized diethyl $^{13}$C fumarate. In a particular embodiment, the hyperpolarized diethyl $^{13}$C fumarate comprises hyperpolarized diethyl 1,4-$^{13}$C fumarate. Diethyl fumarate is a neutral molecule, can be used at physiological pH, and crosses biological membranes. Diethyl fumarate can be incorporated into cells in tissue culture, and is metabolized in the TCA cycle. In addition, diethyl fumarate is non-toxic.

In one embodiment, hyperpolarized dialkyl $^{13}$C fumarate is useful for metabolic imaging of a patient. In one embodiment, a method for metabolic imaging of a patient using hyperpolarized dialkyl $^{13}$C fumarate is provided, the metabolic imaging comprising: administering to the patient a diagnostically effective amount of a composition comprising hyperpolarized dialkyl $^{13}$C fumarate; and detecting hyperpolarized metabolic products in the patient.

The term "patient" includes both human and non-human mammals. The phrase "diagnostically effective amount" means an amount of hyperpolarized dialkyl $^{13}$C succinate or hyperpolarized dialkyl $^{13}$C fumarate, which, when used in a diagnostic method, apparatus, or assay, is sufficient to achieve the desired diagnostic effect or the desired biological activity necessary for the diagnostic method, apparatus, or assay. Such an amount would be sufficient to elicit the biological or medical response in a diagnostic method, apparatus, or assay, which may include a biological or medical response in a patient or in an in vitro or in vivo tissue or system that is sought by a researcher or clinician. The amount of hyperpolarized dialkyl $^{13}$C succinate or hyperpolarized dialkyl $^{13}$C fumarate that constitutes a diagnostically effective amount will vary depending on such factors as the diagnostic method, apparatus, or assay used, the composition used for administration, the time of administration, the route of administration, the rate of excretion of the compound, the duration of administration, drugs and other compounds used in combination with or coincidentally with the compounds of the invention, and, if a patient is the subject of the diagnostic administration, the age, body weight, general health, sex, and diet of the patient. Such a diagnostically effective amount can be determined routinely by one of ordinary skill in the art having regard to their own knowledge, the prior art, and this disclosure.

In one embodiment, hyperpolarized diethyl 1-$^{13}$C 2,3-d$_2$ succinate may be prepared by hydrogenation of diethyl 1-$^{13}$C 2,3-d$_2$ fumarate. FIG. 1A illustrates an example schematic for the hydrogenation of diethyl 1-$^{13}$C 2,3-d$_2$ fumarate to diethyl 1-$^{13}$C 2,3-d$_2$ succinate with pH$_2$ using a rhodium bisphosphine catalyst.

PHIP uses pH$_2$ gas to hydrogenate a $^{13}$C- (or $^{15}$N-) labeled unsaturated organic molecule (an alkyne or an alkene). A catalyst is used to transfer the hydrogens as a unit on the compound without scrambling the spin state.

Figure 1B:
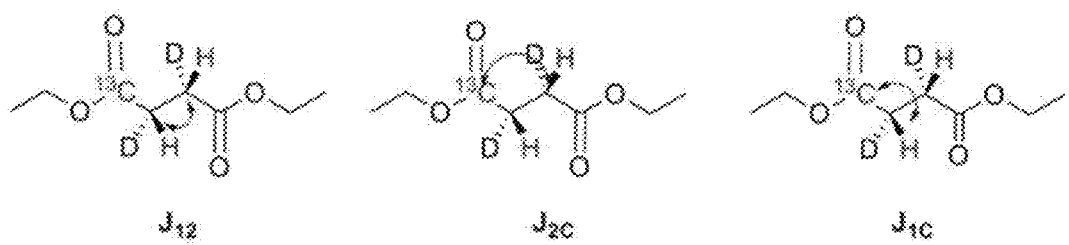
FIG. 1B depicts example coupling constants of diethyl 1-$^{13}$C 2,3-d$_2$ succinate for creating a radio frequency heteronuclear pulse for polarization transfer to the $^{13}$C atom.
Figure 1C:
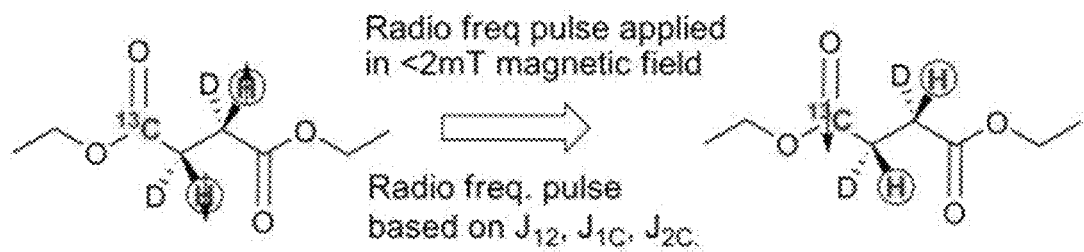
FIG. 1C illustrates an example schematic of the polarization transfer from the pH$_2$ to the $^{13}$C nucleus using a radio frequency pulse applied in a low magnetic field.
Figure 1D:
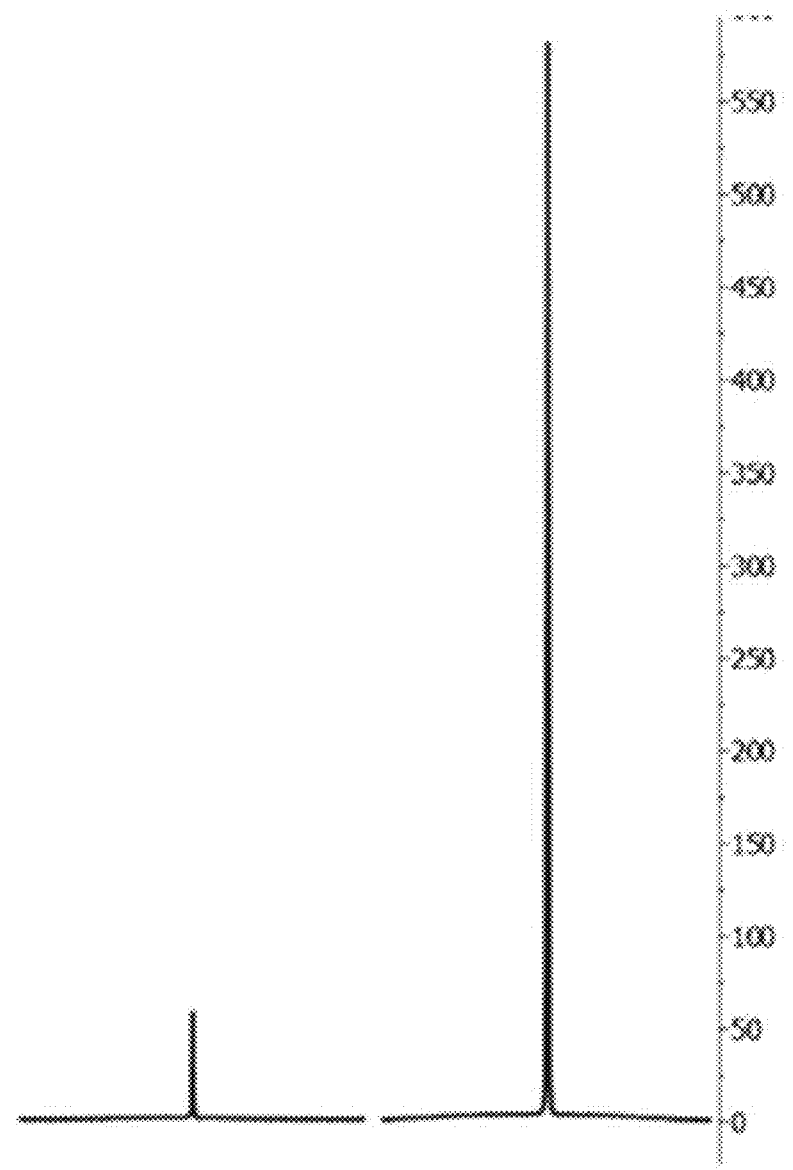
FIG. 1D illustrates an example magnitude of a 20 mM hyperpolarized diethyl 1-$^{13}$C 2,3-d$_2$ succinate signal compared to that from a 3 M 1-$^{13}$C acetate phantom.

With further specific respect to diethyl 1-$^{13}$C 2,3-d$_2$ succinate, the spin order may be transferred from the $^1$H nuclei to the $^{13}$C labeled carbonyl using radio frequency pulses. Changes in the pulse width, amplitude, and timing between the proton and carbon radio frequency pulses affect the percentage of polarization that is transferred to the $^{13}$C. FIG. 1B depicts example coupling constants of diethyl 1-$^{13}$C 2,3-d$_2$ succinate for creating a radio frequency heteronuclear pulse for polarization transfer to the $^{13}$C atom. FIG. 1C illustrates an example schematic of the polarization transfer from the pH$_2$ to the $^{13}$C nucleus using a radio frequency pulse applied in a low magnetic field. The polarization percentage increased from 0.19±0.06% to 2.1 (a 5,000 fold signal enhancement compared to Boltzmann polarization) by systematically changing the pulse sequence. FIG. 1D illustrates an example magnitude of a 20 mM hyperpolarized diethyl 1-$^{13}$C 2,3-d$_2$ succinate signal compared to that from a 3 M 1-$^{13}$C acetate phantom. Each spectrum was taken on a 4.7 T MR scanner using a single pulse and acquire method using a 45° flip angle.

PHIP polarization on a $^{13}$C compound relaxes at a rate defined by T$_1$. The spin lattice relaxation time for hyperpolarized diethyl $^{13}$C succinate in a syringe and in vivo was measured on a 4.7 T MR scanner by measuring the decay of the polarized carbon signal using a single 10° pulse every six seconds for a total of 32 scans and a total of 3.2 minutes. The T$_1$ of the labeled carbonyl is 38±4 seconds in vivo and 54±2 seconds in a syringe in a 9:1 ratio of water to D$_2$O solution of 20 mM hyperpolarized diethyl 1-$^{13}$C 2,3-d$_2$ succinate. The T$_1$ is significantly lower when polarization occurs in 100% water (24 s, in vivo). The 9:1 mixture of water and D$_2$O solvent mixture was used in all in vivo experiments. The pH of 20 mM diethyl $^{13}$C fumarate in 9:1 water to D$_2$O catalyst solution is 8. After hydrogenation, the pH is 6.

Hyperpolarized diethyl 1-$^{13}$C 2,3-d$_2$ succinate has been synthesized, polarized, and imaged, as disclosed herein. After experimentally determining the coupling constants of hyperpolarized diethyl 1-$^{13}$C 2,3-d$_2$ succinate in aqueous solution and generating heteronuclear radio frequency pulse sequences, diethyl succinate can be hyperpolarized via PHIP in an aqueous solution with signal enhancement of 5,000 compared to Boltzmann polarization. The hyperpolarized solution can be generated at four minute intervals with complete conversion to hyperpolarized diethyl 1-$^{13}$C 2,3-d$_2$ succinate.

The T$_1$ of hyperpolarized $^{13}$C-labeled carbonyl in diethyl succinate was determined to be 38 s in vivo, which allows for the signal to be measured for over 3 min. $^{13}$C MRS and MRI were achieved in vivo using tail vein and intraperitoneal injections of 20 mM hyperpolarized diethyl 1-$^{13}$C 2,3-d$_2$ succinate into normal mice. Metabolism of hyperpolarized diethyl 1-$^{13}$C 2,3-$d_2$ succinate was seen in all injections. Based on $^{13}$C MRS TCA cycle metabolite phantoms, the spectral peaks of the hyperpolarized diethyl 1-$^{13}$C 2,3-$d_2$ succinate have been assigned to be malate, succinate, fumarate, and aspartate.

The metabolism of diethyl $^{13}$C succinate was altered after exposing the animal to 3-nitropropionate, a known irreversible inhibitor of succinate dehydrogenase.

Based on these results, it has been shown that PHIP-induced hyperpolarized diethyl 1-$^{13}$C 2,3-$d_2$ succinate allows for ultra-fast in vivo MRI and MRS with a high signal to noise ratio, and multiple enzyme catalyzed reactions can be visualized.

Dialkyl $^{13}$C succinate and dialkyl $^{13}$C fumarate may be hyperpolarized either by PHIP or DNP method. The diethyl 1-$^{13}$C 2,3-$d_2$ succinate examples disclosed herein have been performed using PHIP method of hyperpolarization. Twenty different samples of hyperpolarized diethyl $^{13}$C succinate may be generated in a single day in vivo imaging experiment. However, it is not the intention to restrict or in any way limit the scope of the appended claims to such detail. For clinical purposes, either polarization method may be used.

In one embodiment, hyperpolarized dialkyl $^{13}$C succinate and dialkyl $^{13}$C fumarate may be useful to study metabolism in cancer animal models versus normal animals. In another embodiment, hyperpolarized dialkyl $^{13}$C succinate and dialkyl $^{13}$C fumarate may be useful to compare metabolism in normal animals versus neurodegenerative disease animal models. In another embodiment, hyperpolarized dialkyl $^{13}$C succinate and dialkyl $^{13}$C fumarate may be useful to compare metabolism in normal animals versus heart disease animal models.

Hyperpolarized dialkyl $^{13}$C succinate and dialkyl $^{13}$C fumarate may be useful in clinical metabolic imaging and spectroscopy, and in exploring the metabolic differences in the TCA cycle in both disease and normal tissue in animal models, providing a real-time metabolic fingerprinting of different types of cancer and tumor-specific oncogene expressions, neurodegenerative disorders, and heart disease.

In one embodiment, hyperpolarized dialkyl $^{13}$C succinate or dialkyl $^{13}$C fumarate may be administered to a patient with subsequent MRI/MRS in order to establish a baseline spectrum of the patient's normal TCA cycle metabolism of hyperpolarized dialkyl$^{13}$C succinate or dialkyl $^{13}$C fumarate. In one embodiment, the patient is healthy when the baseline spectrum is established. Thus, subsequent administration to the patient of hyperpolarized dialkyl $^{13}$C succinate or dialkyl $^{13}$C fumarate may be used, for example, to determine deviations from the baseline spectrum indicative of a disease state. In another embodiment, the patient may already have been diagnosed with a disease known or suspected to alter the patient's normal TCA cycle metabolism of hyperpolarized dialkyl $^{13}$C succinate or dialkyl $^{13}$C fumarate. In that case, subsequent administration to the patient of hyperpolarized dialkyl $^{13}$C succinate or dialkyl $^{13}$C fumarate may be used, for example, to gauge disease progression or to determine the effectiveness of treatment. In another embodiment, hyperpolarized dialkyl $^{13}$C succinate or dialkyl $^{13}$C fumarate may be administered to a patient to guide medical professionals with respect to a course treatment of the patient, e.g., to help the medical professional choose a drug or an amount of a radiation dose for a patient with cancer. For instance, if a tumor seems to be a very reductive tumor (i.e., low TCA cycle metabolism) a higher radiation dose might be used.

In yet another embodiment, the baseline spectrum may reflect a sampling of healthy or diseased patients other than the patient under study. Thus, administration to the patient of hyperpolarized dialkyl $^{13}$C succinate or dialkyl $^{13}$C fumarate may be used, for example, to determine deviations from, or similarities to, the baseline spectrum indicative of a disease state or the absence of a disease state.

In another embodiment, hyperpolarized dialkyl $^{13}$C succinate and dialkyl $^{13}$C fumarate may provide a window to the early response to targeted cancer therapy. A successful outcome may be indicated by the appearance, in otherwise predominantly glycolytic tumors, of the intermediates of a (recovered) TCA cycle. In still another embodiment, hyperpolarized dialkyl $^{13}$C succinate and dialkyl $^{13}$C fumarate may be useful to reveal a local status of TCA cycle metabolism, interrogate the same, and monitor therapy in diseases on the time scale of seconds to minutes with unprecedented chemical specificity and MR sensitivity.

EXAMPLES

Certain embodiments are described below in the form of examples. It is impossible to depict every potential application of the invention. Thus, while the embodiments are described in considerable detail, it is not the intention to restrict or in any way limit the scope of the appended claims to such detail, or to any particular embodiment.

Example 1

Preparation of PHIP-Induced Hyperpolarized Diethyl 1-$^{13}$C 2,3-$d_2$Succinate Parahydrogen Preparation Commercially available ultra pure hydrogen (Gilmore, South El Monte, USA) was catalytically converted to p$H_2$ by slow passage over granular hydrous ferric oxide (IONEX-type O-P catalyst; Molecular Products Inc., Lafayette, Colo., USA) at a temperature of 36-55° K. After the gas was converted to p$H_2$, it was stored in 7 L aluminum cylinders at room temperature at a pressure of 33 bar. The quality of pH2 was determined to be >97% by high resolution NMR. Each batch was used within two days, during which there was no measurable decrease in the yield.

Synthesis of Diethyl 1-$^{13}$C 2,3-$d_2$ Fumarate

In a dry 150 ml round bottom flask equipped with a stir bar, 1 g (8.44 mmol) of 1-$^{13}$C fumaric acid was added. 60 ml of anhydrous ethanol and 3.2 ml (25.2 mmol) of chlorotrimethylsilane (386529, Sigma-Aldrich, St. Louis, Mo.) was added via syringe into the reaction. The reaction was stirred under an inert atmosphere at room temperature overnight. The reaction was quenched with 20 ml of saturated sodium bicarbonate. Solid bicarbonate was added until the reaction mix became neutral. The reaction mix was filtered to remove excess bicarbonate. Ethanol was removed by rotary evaporation. Diethyl 1-$^{13}$C 2,3-$d_2$ fumarate was extracted out of the aqueous solution using dichloromethane (3×25 ml). Organic layers were combined, dried over anhydrous sodium sulfate, and filtered. Dichloromethane was removed by evaporation. Pure diethyl 3-$^{13}$C 4,5-$d_2$ fumarate was isolated as a colorless liquid. 1.10 g (75% yield). $^1$H (CD$_2$Cl$_2$, 500 MHz) δ 4.23 (complex quartet, J=7.1, 1.5, 1.6 Hz, 4H), 1.29 (t, J=7.1 Hz, 6H). Proton-decoupled $^{13}$CNMR (CD$_2$Cl$_2$, 125 MHz) δ 165.43 (s), 133.6 (sextet J=25 Hz, t J=25 Hz), 61.8 (s), 14.43 (s).

Hydrogenation Catalyst

A water soluble rhodium catalyst developed for the purpose of rapid hydrogenation while preserving the desired spin order was freshly prepared by mixing two components. The bisphosphine ligand, 1,4-bis-[(phenyl-3-propane sulfonate)

phosphine]butane disodium salt (Q36333, Isotec, OH, USA) was dissolved in 9:1 water to $D_2O$ to yield an 8.25 mM concentration, followed by removal of oxygen using vacuum and argon purging. The rhodium catalytic moiety was introduced to the reaction mixture as a solution of bis(norbornadiene)rhodium (I) tetrafluoroborate (catalog number 45-0230, Strem Chemicals, MA) in minimal acetone to yield a concentration of 5.5 mM. The resulting solution was vigorously shaken and acetone was removed under vacuum and argon purging at room temperature. Diethyl 1-$^{13}$C 2,3-$d_2$ fumarate was added by injecting the compound neat into the catalyst solution. The syringe was washed twice with catalyst solution by pulling up solution into the syringe and re-injecting it into the catalyst solution to remove all of the diethyl fumarate out of the syringe. The solution of diethyl fumarate and catalyst was filtered through a 0.45 μm cellulose acetate syringe filter (VWR, 28145-481). The filtered solution was quickly taken up in a 30 ml plastic syringe and used for injection of the desired amount of imaging reagent precursor for each experiment (4 ml) into the reaction chamber of the polarizer.

A full description of equipment suitable for use to develop high levels of $^{13}$C polarization using parahydrogen is provided in Hovener, J. B.; Chekmenev, E. Y.; Harris, K. C.; Perman, W. H.; Robertson, L. W.; Ross, B. D.; Bhattacharya, P. MAGMA 2009, 22, 111-21, and in Hovener, J. B.; Chekmenev, E. Y.; Harris, K. C.; Perman, W. H.; Tran, T. T.; Ross, B. D.; Bhattacharya, P. MAGMA 2009, 22, 123-34, both of which are incorporated by reference herein in their entireties.

Most hydrogenations were done at 60° C. with 12 bar parahydrogen gas and using 15 bar nitrogen to remove the hyperpolarized compound from the reaction chamber. Hydrogenation was complete using these conditions. Aliquots of the hydrogenation reactions were analyzed on a Varian 11.7 T NMR instrument, and $^{13}$C spectroscopy was performed. The $^{13}$C spectroscopy for the catalyst and diethyl $^{13}$C fumarate solution is different before and after hydrogenation. The change in the carbonyl chemical shift from 167.4 ppme (corresponding to diethyl fumarate) to 175.7 ppm (corresponding to diethyl succinate) is easily seen. A resonance at 167.4 ppm was not seen in any of the reactions tested. Aliquots of 0.5 ml of hyperpolarized, hydrogenated $^{13}$C reagent was injected into the mouse via tail vein. In a few experiments, aliquots of 1 ml of hyperpolarized hydrogenated reagent were injected into a mouse's intraperitoneal cavity.

Example 2

Representative Conditions for Use of Diethyl $^{13}$C Succinate in Metabolic Imaging MR Scanner and Coils All MRI imaging and MRS of animals or phantoms were performed in an animal 4.7 T MR scanner (Bruker Avance, Bruker AG, Germany) horizontal bore using a $^1$H/$^{13}$C full body mouse volume coil (Doty Scientific, South Carolina, USA), unless otherwise noted. For rat studies, a $^1$H/$^{13}$C dual resonance 4 cm ID solenoid volume coil was utilized for $^{13}$C hyperpolarized in vivo imaging and spectroscopy.

Animals

Different sets of animals have been used in the examples below illustrating the utility of hyperpolarized diethyl succinate metabolic imaging. All animal experiments were approved by the IACUC of Huntington Medical Research Institutes. All animals were anesthetized with 2.0-2.5% isoflurane gas with 0.8 L/min oxygen per face mask. Male BALB/c mice were purchased from Harlan S/D and on average weighed 25 grams. Thirteen of these mice were used as is and are described in the examples below as normal mice. Other BALB/c mice were implanted with 5×10$^6$ cells from one of three mouse cancer lines: RENCA (renal carcinoma), A20 lymphoma, and 4T1 (breast). These animals are described in the examples below as allograft tumor bearing mice. For tail vein injections, the lateral tail vein was catheterized with 30-gauge tubing (MVT-1, Braintree Scientific), attached to a two-foot PESO extension. A warm-water tail bath produced the vasodilation critical to successful cannulation. The sedated mouse was placed in a heated cradle within the bore of the MR scanner.

For mice experiments that required an intraperitoneal (i.p.) catheter, the anesthetized mouse was subjected to one of two procedures: laparotomy or needle puncture. The laparotomy technique involved a small (2-4 mm) mid-sagittal abdominal incision through skin and peritoneum while the mouse laid supine. The tip of a two foot PESO catheter was placed in the intraperitoneal space under direct visualization. Silk sutures anchored the catheter to the skin as well as closed the wound. Alternatively, i.p. access was affected by passing the PESO catheter through an 18 gauge needle after a blind, transcutaneous puncture. The abdominal skin was tented upward to avoid visceral injury. Once the needle was withdrawn over the catheter, no suture was necessary to prevent leaks. After either procedure, the mouse was carefully pronated and placed in the magnet.

Measuring Polarization

The polarization of diethyl $^{13}$C succinate was measured (25 s to 40 s after polarization) in a plastic syringe using $^{13}$C spectroscopy with a single scan pulse and acquire sequence using a pulse angle of 45° in the MR scanner. To quantify the degree of hyperpolarization, reference was made to a single scan spectrum of thermally polarized 3 M 1-$^{13}$C acetate phantom at 4.7 T using the following formula:

$$\%P_{t=detection} = \frac{[\text{reference}]}{[\text{polarized}]} * \frac{\text{signal(polarized)}}{\text{signal(reference)}} * \frac{100\%}{246,600}$$

where 1/246,600 corresponds to $^{13}$C. nuclear polarization at 298° K and at 4.7 T, according to the Boltzmann distribution. The degree of hyperpolarization produced in the PHIP polarizer at time zero was back calculated, using the delivery time and spin-lattice relaxation time $T_1$ of the hyperpolarized agent as follows:

$$\%P_{t=0} = \%P_{t=detection} * \exp\left(\frac{\text{delivery time}}{T_1}\right)$$

The reported % hyperpolarization refers to % $P_{t=0}$.

$^1$H MRI

Proton anatomic images for mice were obtained with a dual tuned volume coil to allow co-registration of carbon hyperpolarized images with mouse anatomic images. RARE (rapid acquisition with relaxation enhancement) tri-pilot was used for placement of the animal and MSME (multi-slice multi-echo) coronal imaging using a range of slice thicknesses (4.5, 7.5, or 15.2 mm) and a FOV of either 6 or 7 cm were used for co-registration of carbon hyperpolarized images. Magnetic field homogeneity was adjusted using a single voxel proton MRS ((PRESS) point resolved spectroscopy) data acquisition approach, and the voxel (0.7×0.7×0.7 cm) of interest was placed just posterior of the kidneys in the animal. An unsuppressed water signal less than 15 Hz was routinely obtained. Shimming was used for peak resolution in $^{13}$C MRS experiments.

$^{13}$C MRS

Two to three successive injections of hyperpolarized reagent ($^{13}$C diethyl succinate) were performed, optimizing the use of the rapidly decaying hyperpolarized $^{13}$C MR signal in order to obtain information on both anatomic distribution and metabolism of diethyl $^{13}$C succinate. Consecutive $^{13}$C MRS was acquired using a pulse and acquire approach (bandwidth 25,000 Hz and acquisition size 2,048) every 7-8 seconds for about 1 minute after injection of hyperpolarized diethyl $^{13}$C succinate into the mouse, and using a non-selective Gaussian radio frequency pulse for excitation, and a pulse angle of 30°.

Spectroscopy was done before or after a $^{13}$C FISP image was taken. Assignments of the $^{13}$C spectroscopy peaks were determined using experimentally determined chemical shift values of metabolites in a D$_2$O/water solution at known pH. The FID raw data was processed either in XwinNMR or MestraNova, using baseline correction (Berstein Polynomial Fit), line broadening of 5 Hz, manual phasing, and with reference to the large diethyl succinate peak at 176.4 ppm.

$^{13}$C CSI $^{13}$C CSI was performed with a 1 ms gauss pulse, 200 ms TR, 8×8 or 16×16 matrix, FOV ranging from 2.64 cm to 4 cm, slice thickness of 9 to 12 mm was used. CSI was processed using 3DiCSI software (Columbia University, Qui Zhao). The CSI was overlaid on a $^1$H MRI image using the same center placement, FOV, and slice thickness.

$^{13}$C MRI $^{13}$C imaging was done using a Bruker TRUE FISP sequence. The imaging sequence used TR=3.3 ms, TE=1.6 ms, 4 averages, a 32×32 matrix, and a bandwidth of 52,083 Hz. All imaging was done in a 4.7 T MR scanner using Doty volume coil. Flip angles of 80, 60, or 40 degrees were used in the sequence. The gradient rise time of the MR Bruker scanner was 250 µs. Coronal imaging was performed using a FOV of 6 or 7 cm, one to two slices with dimensions of 15.2 mm, and the center slice was always selected to be the same as the proton images. Images were converted into false color in Paravision 3.0.2 Software. Only pixels above a certain intensity were used to remove noise from the signal (See FIGS. 5A and 5B). The image was overlaid on the proton image.

$^{13}$C NMR Spectroscopy $^{13}$C proton decoupled spectroscopy on an 11.7 T Varian instrument was taken of about 30 samples containing solutions of different TCA cycle metabolites at concentrations of around 30 mM in D$_2$O and water solution with 0.5% of methanol in the sample as a chemical shift reference. The pH of the samples was adjusted with 356 mM KOH solution and 50 mM phosphate buffer at pH 7.5, and was measured using a pH meter. All spectroscopy was performed with 64 to 256 transients, a 60° flip angle, a relaxation delay of 10 s, and all spectra were referenced to the methanol peak. Some of the carbonyl assignments for the metabolites and pH of the samples can be seen in Table 1.

| $^{13}$C Chemical Shifts of TCA Cycle Metabolites, Referenced to Methanol at 49.5 ppm | | |
|---|---|---|
| $^{13}$C Chemical Shift in ppm | Compound | pH |
| 183 | Succinate | 7.1, 7.5 |
| 183.03 | Lactate | 6.4 |
| 182.5 | Citrate C6 | 7.0, 7.4 |
| 181.8 | Glutamate | 7.24 |
| 181.6 | Malate C4 | 7.3 |
| 181.35 | Isocitrate C1, C5 | 7.03 |
| 180.66 | Isocitrate C6 | 7.03 |
| 180.4 | Malate C1 | 7.3 |
| 179.7 | Citrate C1, C5 | 7.0, 7.4 |
| 175.8 | Diethyl succinate C3 | 7.7, 7.4 |
| 175.1 | Glutamate | 7.24 |
| 175.24 | Fumarate C1 | 7.3 |
| 174.9 | Glutamine | 7.5 |
| 174.42 | Asparagine | 7.64 |
| 173.91 | Asparagine | 6.9 |
| 135.9 | Fumarate C2 | 7.3 |
| 182 | Succinate | 5.7 |
| 181.4 | Glutamate | 5.3 |
| 180.8 | Malate C4 | 5 |
| 180.5 | Citrate C6 | 5 |
| 178.05 | Asparate | 6 |
| 175.8 | Malate C1 | 5 |
| 177.4 | Citrate C1, C5 | 5 |
| 175.9 | diethyl succinate C3 | 5.7 |
| 175 | Glutamate | 5.3 |
| 174.75 | Aspirate | 6 |
| 174.6 | Fumarate C1 | 5 |
| 174.54 | Glutamine | 5.7 |
| 135.8 | Fumarate C2 | 5 |

Example 3

Metabolism of Hyperpolarized Diethyl $^{13}$C Succinate in Normal Mice

Metabolism of hyperpolarized diethyl $^{13}$C succinate was detected in real time in thirteen mice injected with 10 µmol of hyperpolarized diethyl 1-$^{13}$C 2,3-d$_2$ succinate via tail vein, and in three mice injected with 20 µmol of hyperpolarized diethyl succinate in the peritoneum. Representative $^{13}$C MRS exams of hyperpolarized diethyl 1-$^{13}$C 2,3-d$_2$ succinate metabolism in mice are illustrated in FIGS. 2A-2D and FIGS. 3A and 3B.

All spectroscopy shown was collected using a single 30° pulse and acquire sequence every five to nine seconds, unless otherwise noted. The time values were determined based on the time stamps of the raw data and the amount of time the pulse and acquire sequence takes to complete (~5 s). The time values correspond to the time elapsed between the injection of the hyperpolarized compound and when the spectroscopy was performed. Metabolic products from hyperpolarized diethyl 1-$^{13}$C 2,3-d$_2$ succinate (the largest peak, labeled DS) were detected within five seconds of the injection of the hyperpolarized substance and persisted for approximately one minute. Metabolites are seen almost instantly, and metabolism can easily be monitored. The four distinct resonances are assigned to malate, succinate, fumarate, and asparatate. All spectra are referenced to a diethyl succinate peak (176.4 ppm), which was referenced in phantom experiments to $^{13}$C labeled methanol. In most animals, no signal was seen using $^{13}$C spectroscopy with a single transient if hyperpolarized compound was not injected. $^{13}$C spectra using a single transient in a few non-injected mice have lipid peaks at around 30-35 ppm.

Figure 2A:
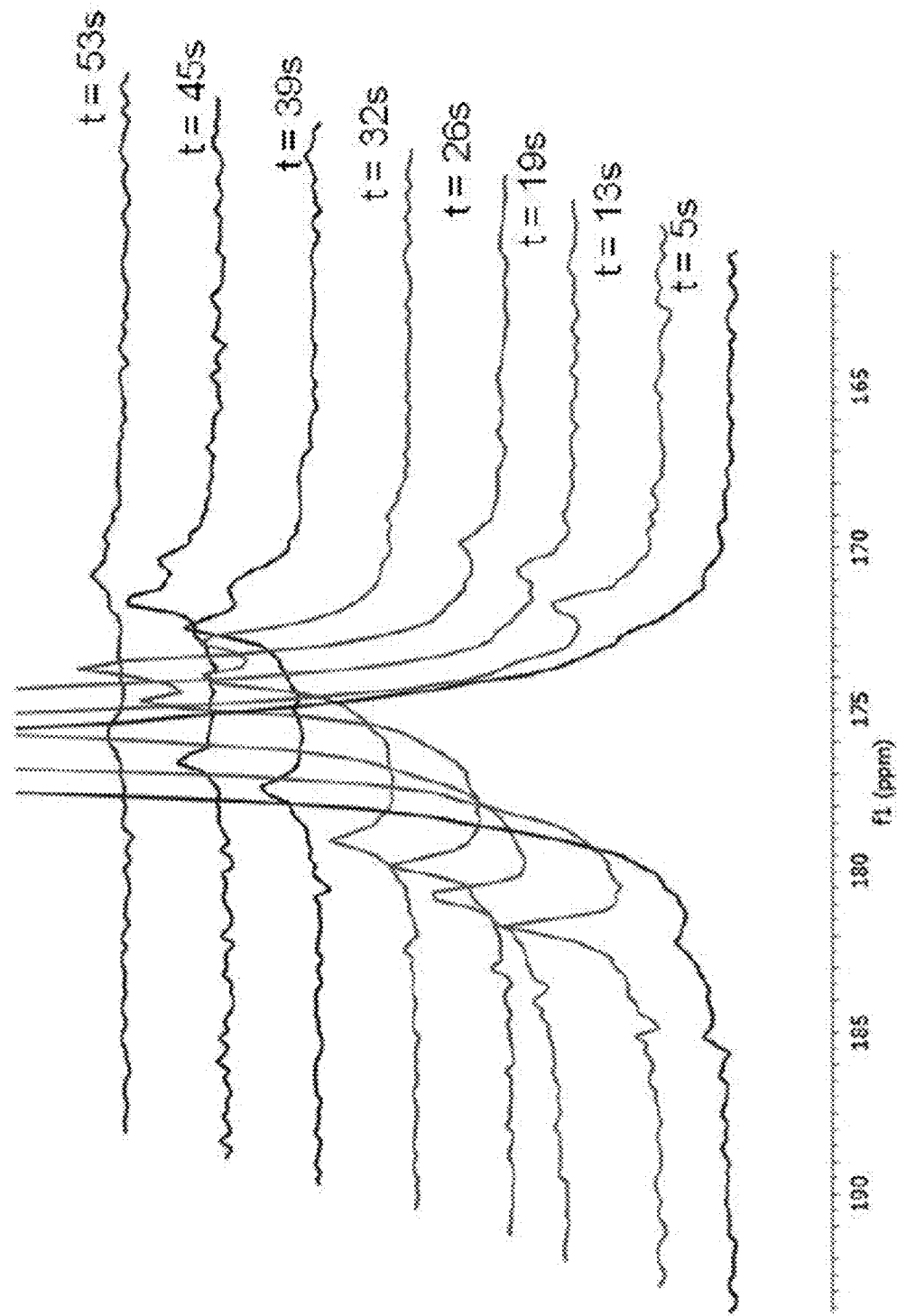
FIG. 2A illustrates an example $^{13}$C MRS time-resolved stackplot as seen in a mouse that received 10 μmol of hyperpolarized diethyl 1-$^{13}$C 2,3-d$_2$ succinate by tail vein injection.

FIG. 2A illustrates an example $^{13}$C MRS time-resolved stackplot as seen in a mouse that received 10 µmol of hyperpolarized diethyl 1-$^{13}$C 2,3-d$_2$ succinate by tail vein injection.

Figure 2C:
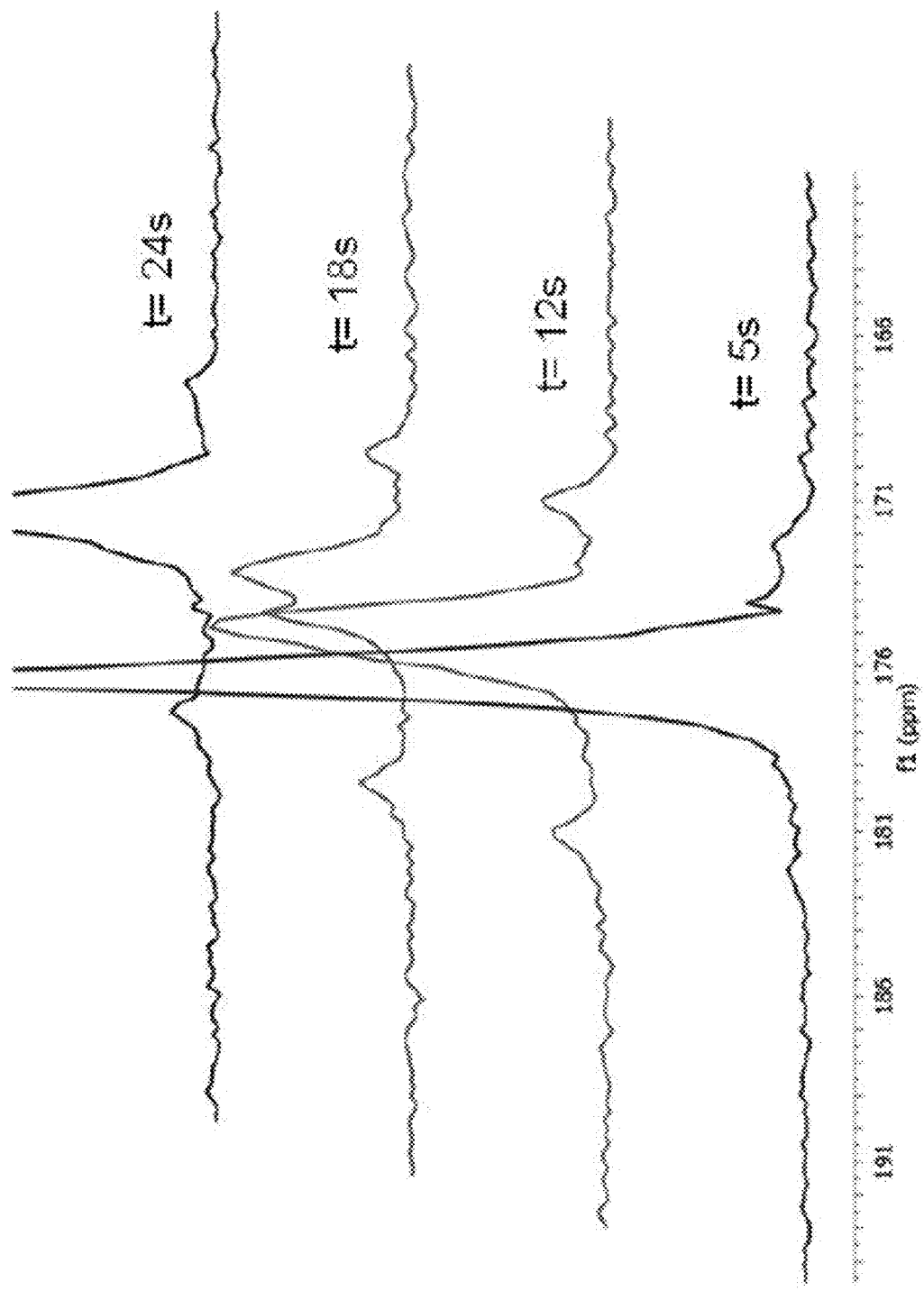
FIG. 2C illustrates an example $^{13}$C MRS time-resolved stackplot as seen in a mouse that received 10 μmol of hyperpolarized diethyl 1-$^{13}$C 2,3-d$_2$ succinate by tail vein injection.
Figure 2D:
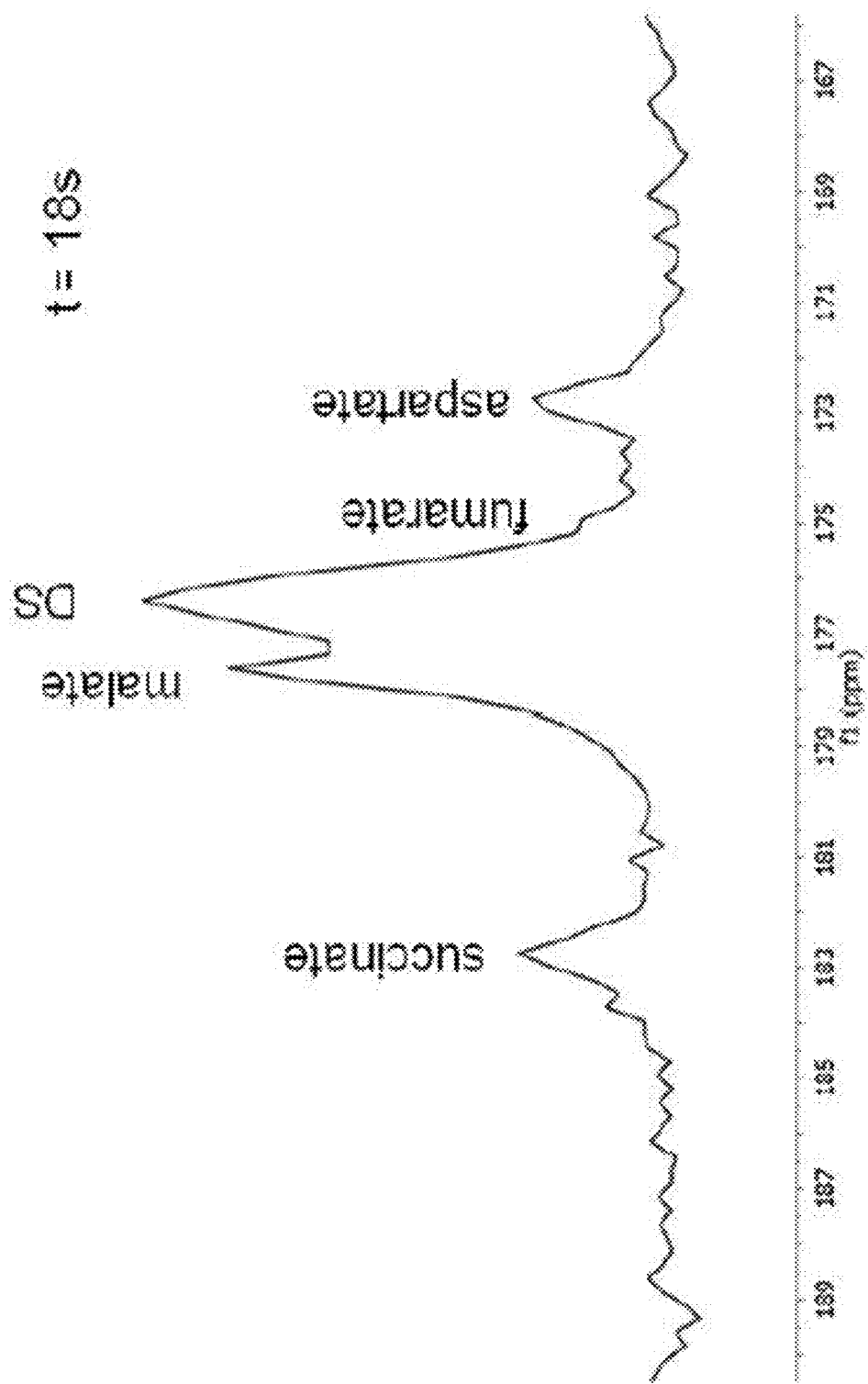
FIG. 2D illustrates an enlarged view of a region of interest of the $^{13}$C MRS acquired at t=18 s as seen in the stackplot of FIG. 2C.

FIG. 2B illustrates an enlarged view of a region of interest of the $^{13}C$ MRS acquired at t=26 s as seen in the stackplot of FIG. 2A. FIG. 2C illustrates an example $^{13}C$ MRS time-resolved stackplot as seen in a mouse that received 10 μmol of hyperpolarized diethyl 1-$^{13}C$ 2,3-$d_2$ succinate by tail vein injection. FIG. 2D illustrates an enlarged view of a region of interest of the $^{13}C$ MRS acquired at t=18 s as seen in the stackplot of FIG. 2C.

Figure 3A:
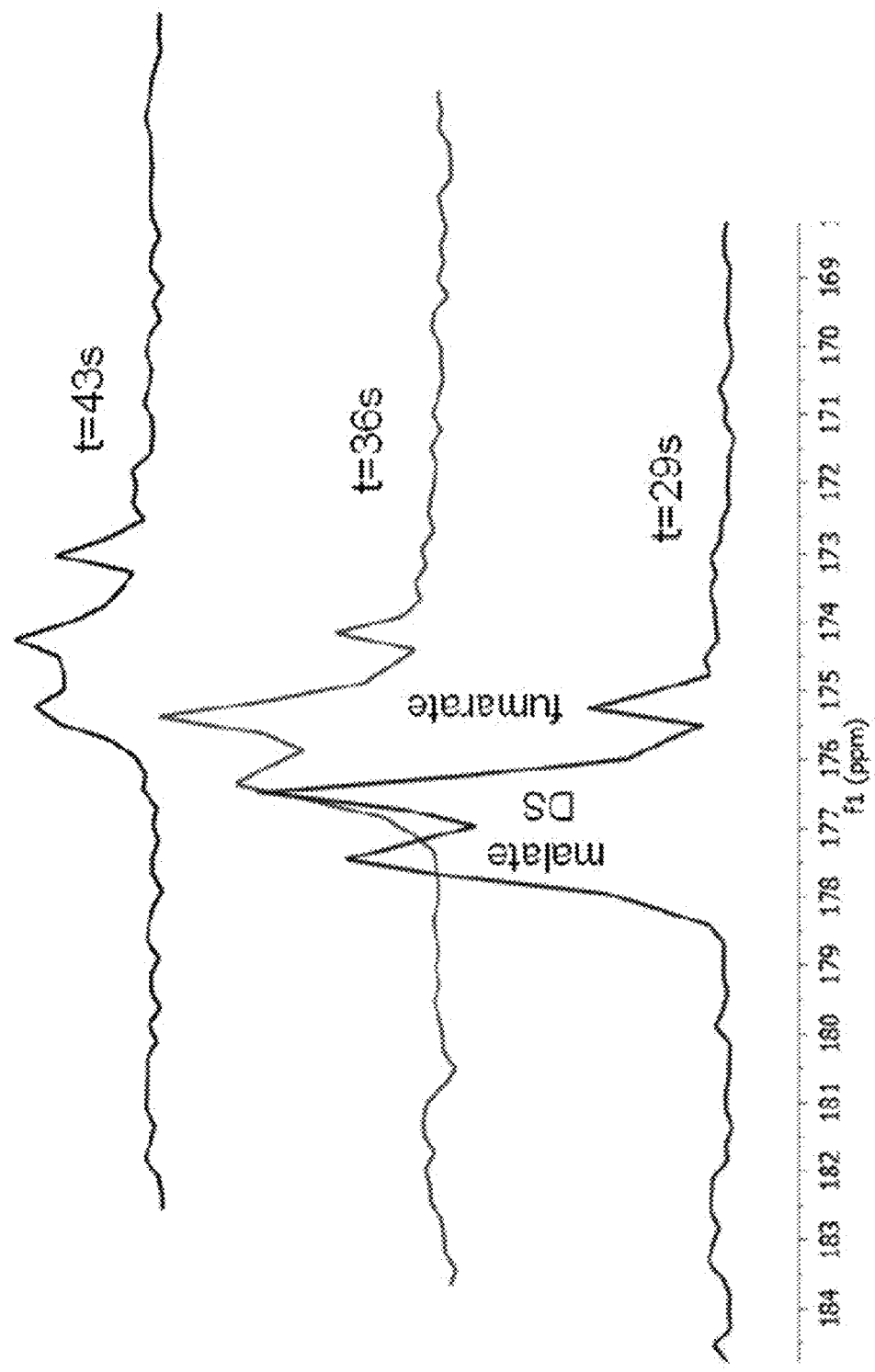
FIG. 3A illustrates an example $^{13}$C MRS time-resolved stackplot as seen in a mouse that received 20 μmol of hyperpolarized diethyl 1-$^{13}$C 2,3-d$_2$ succinate by peritoneum injection.
Figure 3B:
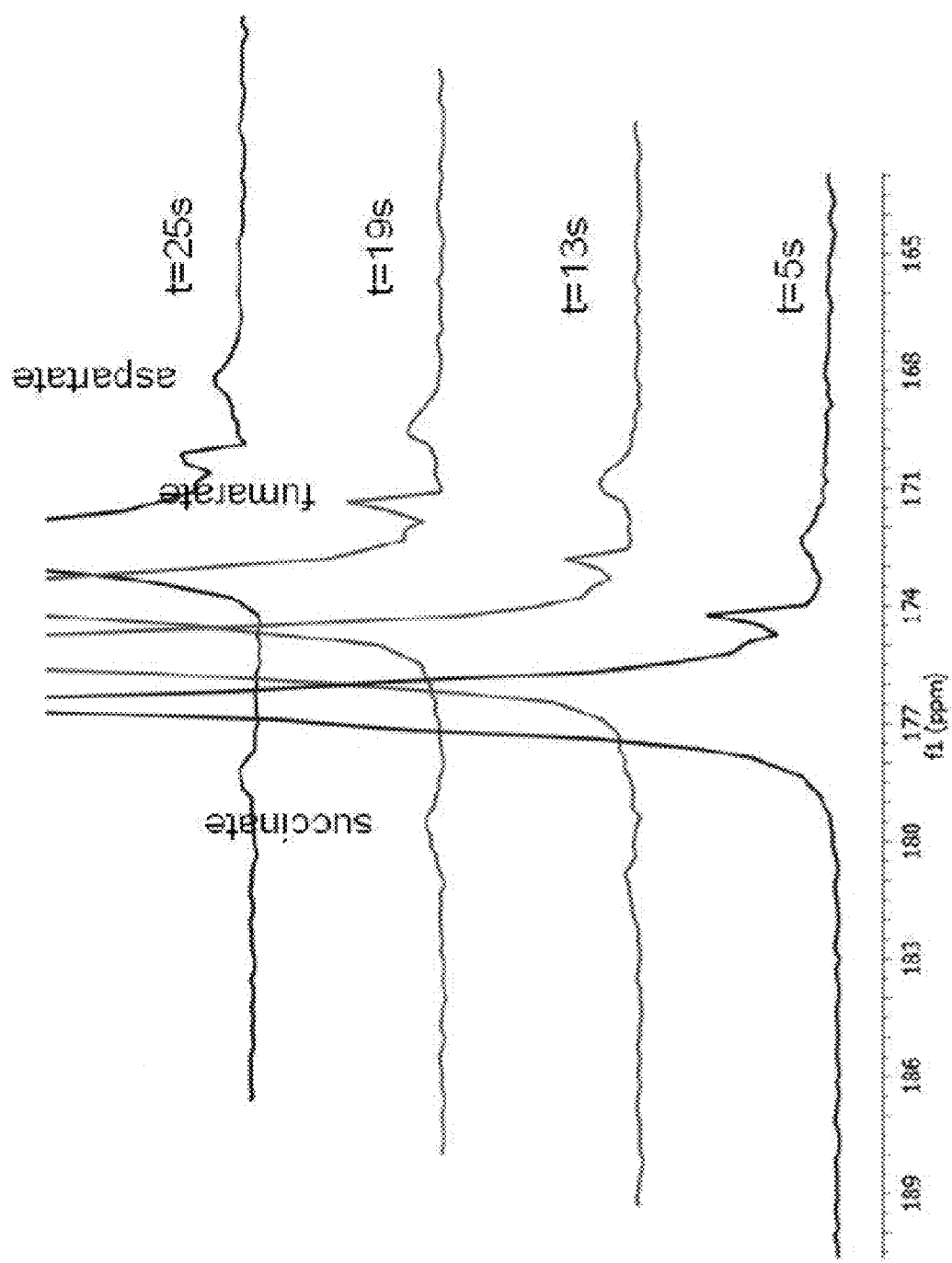
FIG. 3B illustrates an example $^{13}$C MRS time-resolved stackplot as seen in a mouse that received 20 μmol of hyperpolarized diethyl 1-$^{13}$C 2,3-d$_2$ succinate by peritoneum injection.

FIG. 3A illustrates an example $^{13}C$ MRS time-resolved stackplot as seen in a mouse that received 20 μmol of hyperpolarized diethyl 1-$^{13}C$ 2,3-$d_2$ succinate by peritoneum injection. FIG. 3B illustrates an example $^{13}C$ MRS time-resolved stackplot as seen in a mouse that received 20 μmol of hyperpolarized diethyl 1-$^{13}C$ 2,3-$d_2$ succinate by peritoneum injection. To determine the chemical identity of the in vivo metabolites observed, several NMR $^{13}C$ proton-decoupled spectroscopy experiments were performed on a 11.7 T Varian instrument using methanol (49.1 ppm) as a chemical shift reference of samples containing known TCA cycle metabolites in water and $D_2O$ at particular pHs. Although not wishing to be bound by any particular theory, it is hypothesized that, after injection, hyperpolarized diethyl $^{13}C$ succinate is metabolized by esterase in the cell and then metabolized to succinate, aspartate, malate, and fumarate. The pattern of the resonances, as well as the tentative assignments by chemical shift, strongly suggest that hyperpolarized diethyl $^{13}C$ succinate is metabolized in vivo and that its metabolites retain a significant fraction of the hyperpolarized $^{13}C$ nuclei through three or more enzyme-catalyzed biochemical reactions.

Example 4

3-Nitropropionate Inhibition

Qualitative data of the metabolism of hyperpolarized diethyl succinate are useful in the diagnostic imaging of disease states known to have inhibited or unusual TCA cycle metabolism. To further explore the metabolism of hyperpolarized diethyl $^{13}C$ succinate in a mouse, spectroscopy experiments were performed before and after i.p. injection of 3-nitropropionate in four mice. 3-nitropropionate is a known irreversible inhibitor of succinate dehydrogenase. The metabolism of hyperpolarized diethyl $^{13}C$ succinate changes after 3-nitropropionate injection.

Figure 4:
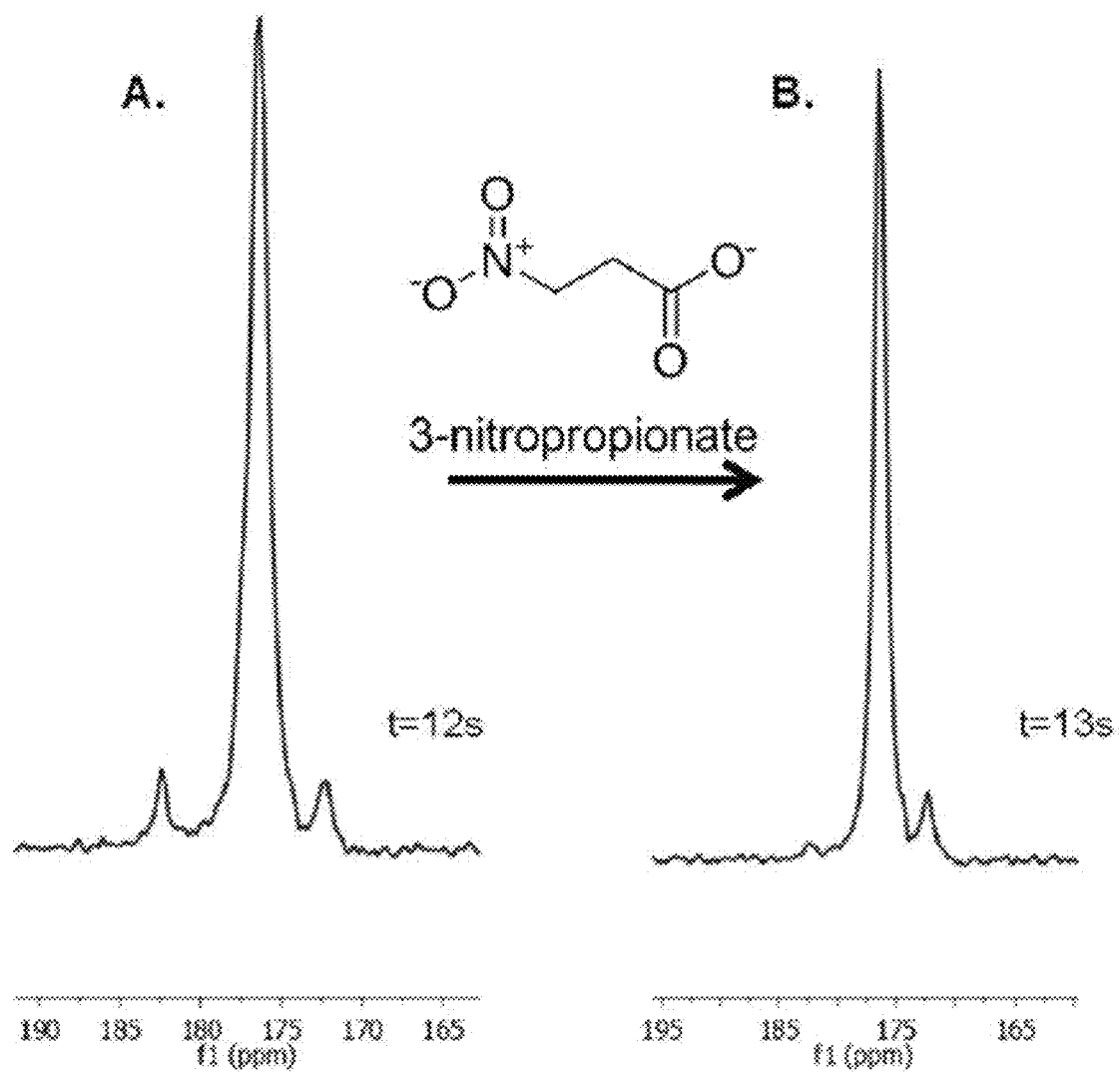
FIG. 4 illustrates example $^{13}$C MRS spectra illustrating hyperpolarized diethyl 1-$^{13}$C 2,3-d$_2$ succinate in a mouse before (spectrum A) and after (spectrum B) the mouse was injected with 3-nitropropionate.

FIG. 4 illustrates example $^{13}C$ MRS spectra illustrating hyperpolarized diethyl 1-$^{13}C$ 2,3-$d_2$ succinate in a mouse before (spectrum A) and after (spectrum B) the mouse was injected with 3-nitropropionate. The mouse was injected with 10 μmol of hyperpolarized diethyl 1-$^{13}C$ 2,3-$d_2$ succinate via i.v. injection before and after a 200 μl injection of a 5 mg/ml solution of 3-nitropropionate (i.p. injection) and a 20 minute wait. The aqueous solution of 5 mg/ml of 3-nitropropionate (Sigma-Aldrich) was brought to a pH of 8.5 using a drop of 50% NaOH solution. Based on chemical shifts, the downfield succinate resonance is significantly reduced in the animal after the 3-nitropropionate treatment. Three out of the four mice had a reduction to complete loss of the succinate peak after the 3-nitropropionate treatment.

Example 5

$^{13}C$ FISP Imaging In Vivo

The relative location of hyperpolarized diethyl 1-$^{13}C$ 2,3-$d_2$ succinate and its metabolites in mice where determined upon injection via the tail vein or into the peritoneum using $^{13}C$ FISP imaging. Images were taken every 9 seconds for up to 1 minute with the TRUE FISP sequence using 60° and 40° flip angles. No $^{13}C$ image was seen if hyperpolarized diethyl 1-$^{13}C$ 2,3-$d_2$ succinate was not injected.

Figure 5D:
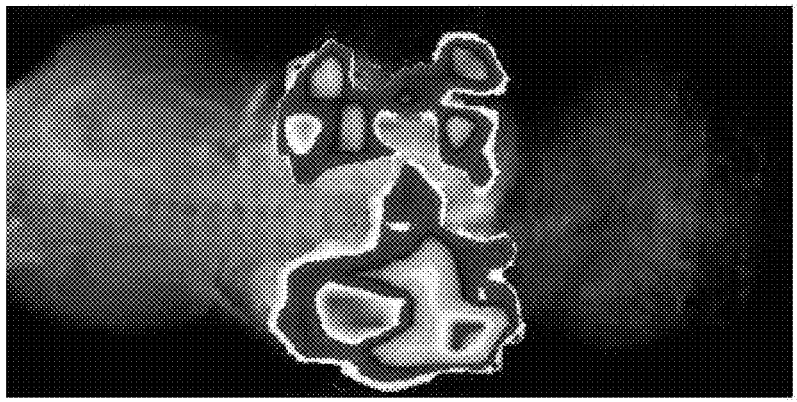
FIG. 5D illustrates example overlays of $^{13}$C FISP images (60° flip angle) taken of a mouse after peritoneum injection of 20 μmol of hyperpolarized diethyl 1-$^{13}$C 2,3-d$_2$ succinate.
Figure 5C:
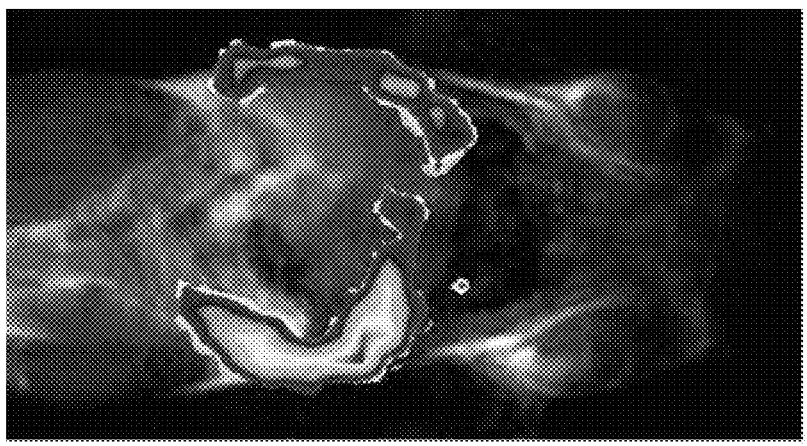
FIG. 5C illustrates example overlays of $^{13}$C FISP images (60° flip angle) taken of a mouse after peritoneum injection of 20 μmol of hyperpolarized diethyl 1-$^{13}$C 2,3-d$_2$ succinate.

FIGS. 5A-5D represent overlays of example $^{13}C$ FISP images in false color over the proton image of the animal using the same FOV and central slice placement. FIG. 5A illustrates example overlays of $^{13}C$ FISP images (60° flip angle) taken of a mouse after intravenous injection of 10 μmol of hyperpolarized diethyl 1-$^{13}C$ 2,3-$d_2$ succinate. FIG. 5B illustrates example overlays of $^{13}C$ FISP images (60° flip angle) taken of a mouse after intravenous injection of 10 μmol of hyperpolarized diethyl 1-$^{13}C$ 2,3-$d_2$ succinate. FIG. 5C illustrates example overlays of $^{13}C$ FISP images (60° flip angle) taken of a mouse after peritoneum injection of 20 μmol of hyperpolarized diethyl 1-$^{13}C$ 2,3-$d_2$ succinate. FIG. 5D illustrates example overlays of $^{13}C$ FISP images (60° flip angle) taken of a mouse after peritoneum injection of 20 μmol of hyperpolarized diethyl 1-$^{13}C$ 2,3-$d_2$ succinate.

Based on the overlays of the images, when hyperpolarized diethyl 1-$^{13}C$ 2,3-$d_2$ succinate is injected intravenously into a mouse, it goes quickly through the cardiovascular system, as seen in FIGS. 5A and 5B where the FISP image is in the location of the heart, and then the hyperpolarized molecule collects in the bladder and ureters (FIG. 5B). With intraperitoneal injection, the hyperpolarized compound and its metabolites stay primarily in the peritoneum (FIGS. 5C and 5D) in the time period tested.

Example 6

Figure 6A:
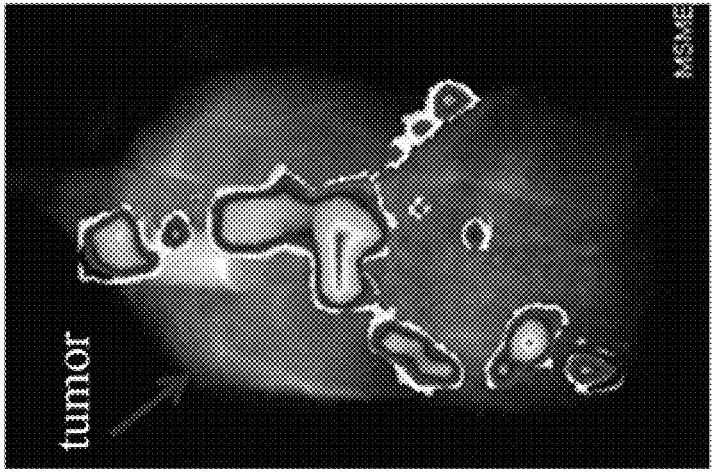
FIG. 6A is a comparison of $^{13}$C FISP images illustrating the biodistribution of hyperpolarized diethyl succinate after intravenous injection of 10 μmol of hyperpolarized diethyl 1-$^{13}$C 2,3-d$_2$ succinate in three different tumor bearing mice: Renal cancer (RENCA) (left image), Lymphoma A20 (center image), and 4T1 breast (right image).
Figure 6A:
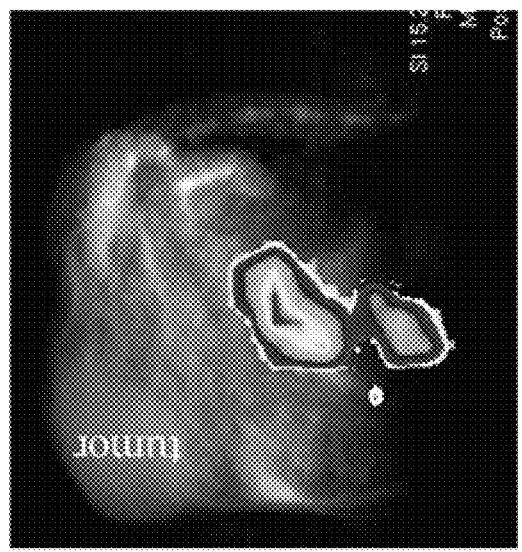
Figure 6A:
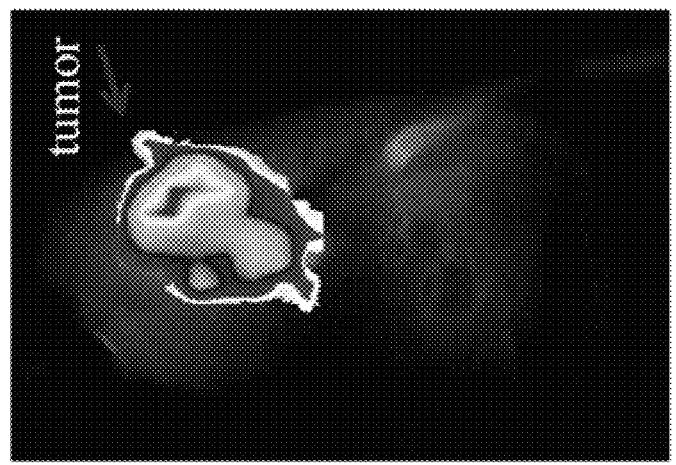
Figure 6B:
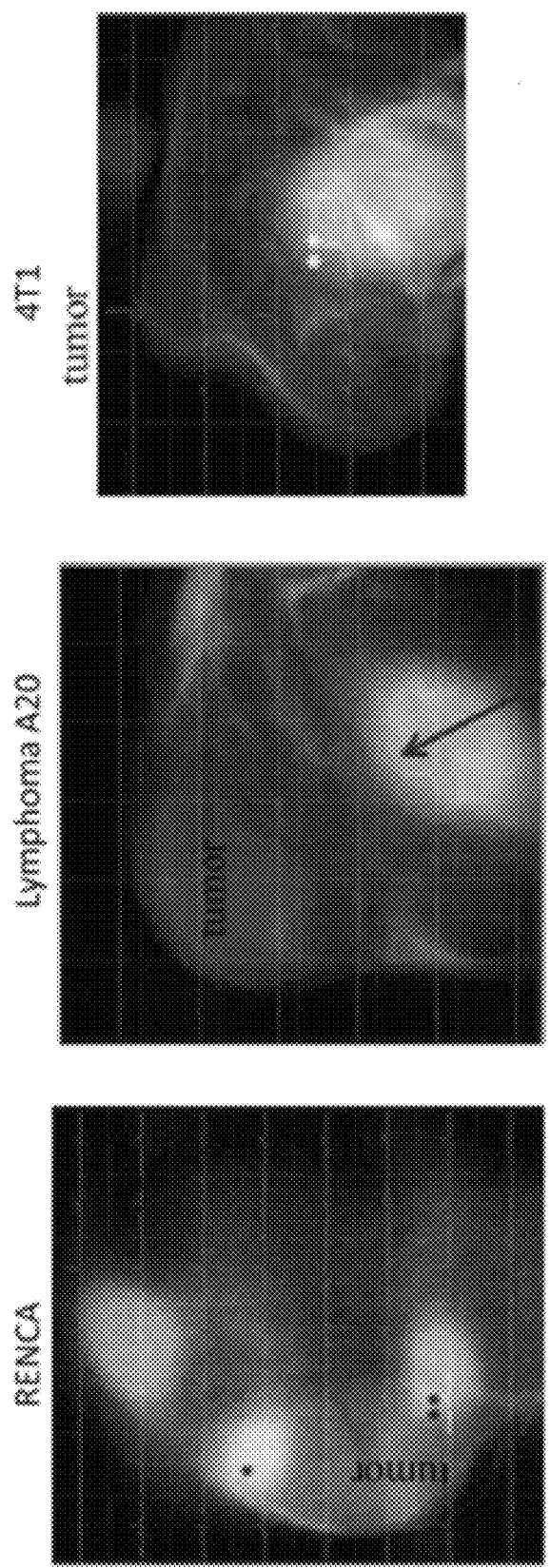
FIG. 6B is a comparison of $^{13}$C CSI images illustrating the majority of hyperpolarized signal through the use of heat map projection after intravenous injection of hyperpolarized diethyl 1-$^{13}$C 2,3-d$_2$ succinate in three different tumor bearing mice: RENCA (left image), A20 Lymphoma (center image), and 4T1 breast (right image).
Figure 6C:
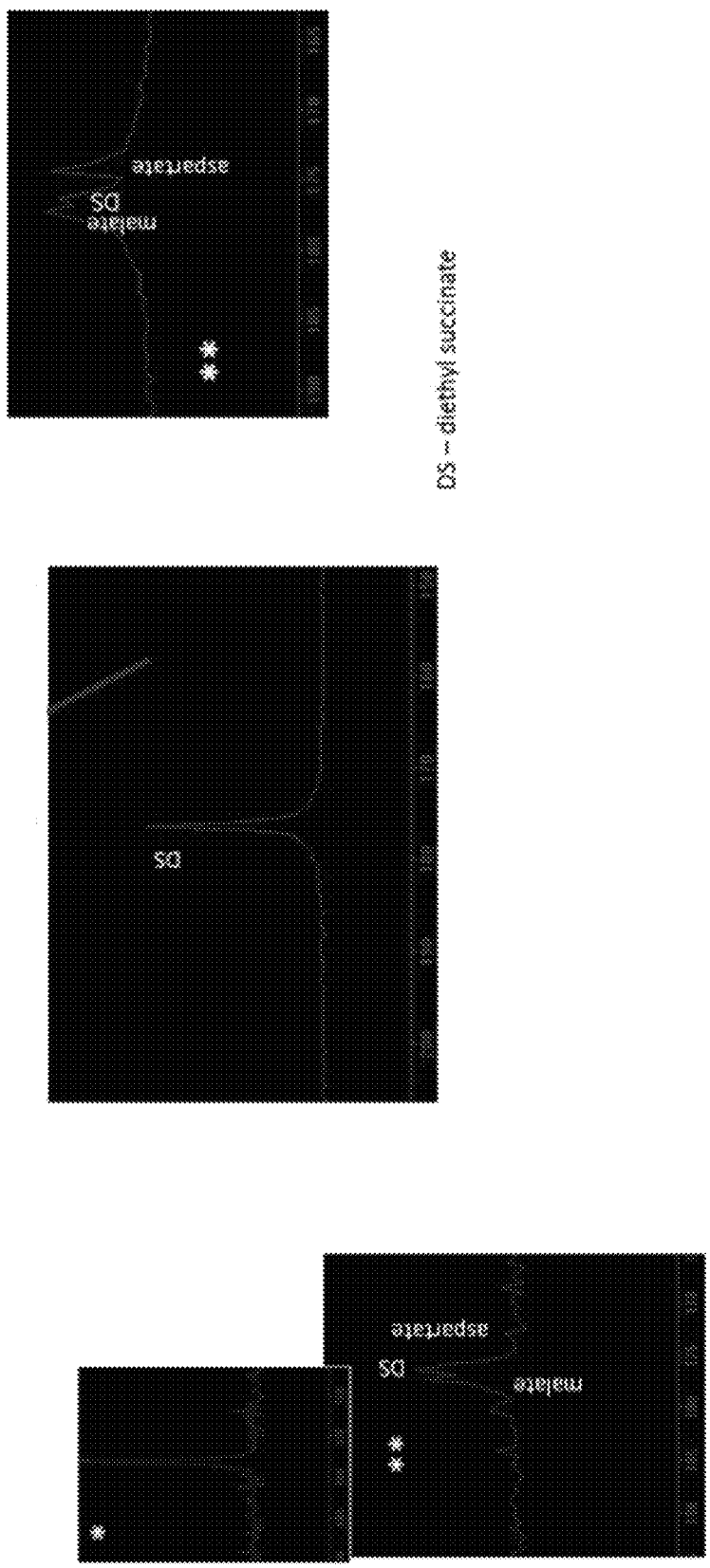
FIG. 6C is a comparison of the metabolic profile of individual voxels within the $^{13}$C CSI images of FIG. 6B, for the three different tumor bearing mice: RENCA (left image), A20 Lymphoma (center image), and 4T1 breast (right image).

Metabolism of Hyperpolarized Diethyl 1-$^{13}C$ 2,3-$d_2$ Succinate in RENCA Tumors, A20 Lymphoma Tumors, and 4T1 Breast Tumors BALB/c mice allograft tumor bearing animals were injected with 10 μmol of hyperpolarized via tail vein. FIG. 6A is a comparison of $^{13}C$ FISP images illustrating the biodistribution of hyperpolarized diethyl succinate after intravenous injection of 10 μmol of hyperpolarized diethyl 1-$^{13}C$ 2,3-$d_2$ succinate in three different tumor bearing mice: Renal cancer (RENCA) (left image), Lymphoma A20 (center image), and 4T1 breast (right image). FIG. 6B is a comparison of $^{13}C$ CSI images illustrating the majority of hyperpolarized signal through the use of heat map projection after intravenous injection of hyperpolarized diethyl 1-$^{13}C$ 2,3-$d_2$ succinate in three different tumor bearing mice: RENCA (left image), A20 Lymphoma (center image), and 4T1 breast (right image). FIG. 6C is a comparison of the metabolic profile of individual voxels within the $^{13}C$ CSI images of FIG. 6B, for the three different tumor bearing mice: RENCA (left image), A20 Lymphoma (center image), and 4T1 breast (right image).

Example 7

Biodistribution and Metabolism of Hyperpolarized Diethyl 1-$^{13}C$ 2,3-$d_2$ Succinate in RENCA Tumors and Breast Cancer (4T1) Tumors Hyperpolarized diethyl succinate was used for imaging cancer in two different subcutaneous tumor models in mice. PHIP was used to hyperpolarize diethyl 1-$^{13}C$ 2,3-$d_2$ succinate. The hyperpolarized solution in near physiological concentrations (10-20 μmol) was injected via the tail vein of BALB/c mice bearing a breast (4T1) (N=5) or renal tumor (RENCA) (N=9). A $^1H/^{13}C$ dual resonance volume coil (Doty Scientific, Inc., Columbia, S.C.) was utilized for $^{13}C$ hyperpolarized in vivo imaging and CSI spectroscopy. $^{13}C$ FISP with a flip angle of 60°, FOV 6 or 7 cm, and slice thickness of 15.2 mm was used. $^{13}$C CSI (1 ms gauss pulse, 200 ms TR, 8×8 or 16×16 matrix, FOV ranging from 2.64 cm to 4 cm, slice thickness of 8 to 12 mm). CSI was processed using 3DiCSI software (Columbia University, Qui Zhao). The flux rate of the compound within the tumor was determined using a 4 cm ID solenoid volume coil and a simple pulse and acquire $^{13}$C sequence. All $^{13}$C imaging and spectroscopy was done on a horizontal bore Bruker Avance 4.7T animal scanner.

Figure 7B:
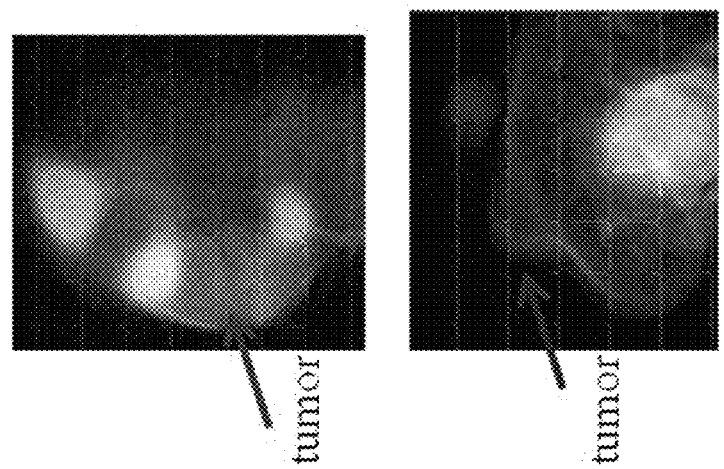
FIG. 7B is a comparison of $^{13}$C CSI images illustrating the biodistribution of hyperpolarized diethyl 1-$^{13}$C 2,3-d$_2$ succinate after intravenous injection in a RENCA tumor (top image) and in a breast tumor (bottom image) of two different mice.
Figure 7A:
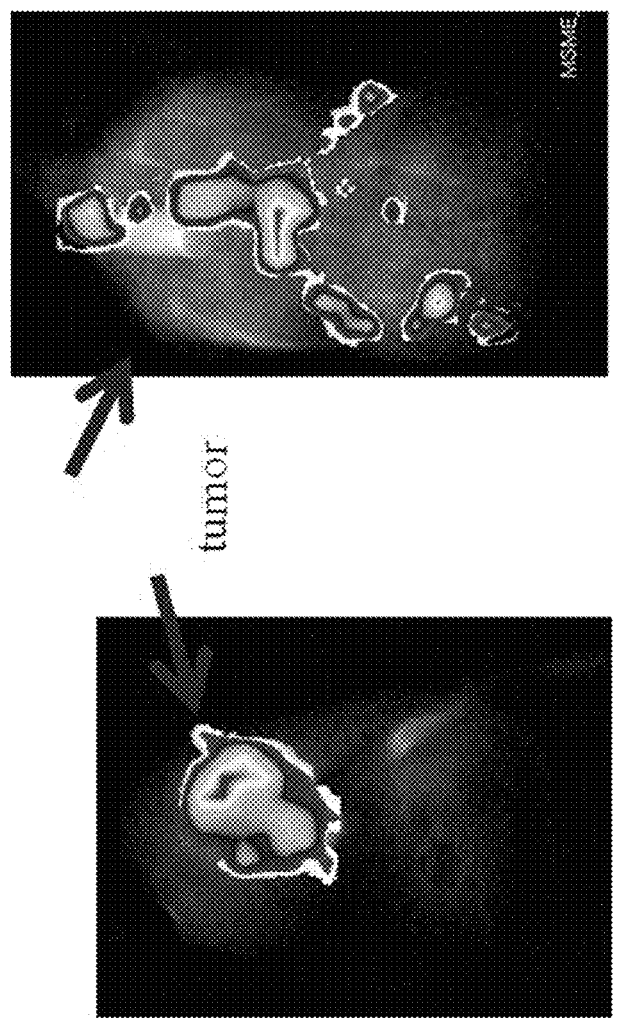
FIG. 7A is a comparison of $^{13}$C FISP images illustrating the biodistribution of hyperpolarized diethyl 1-$^{13}$C 2,3-d$_2$ succinate after intravenous injection in a RENCA tumor (left image) and in a breast tumor (right image) of two different mice.
Figure 7C:
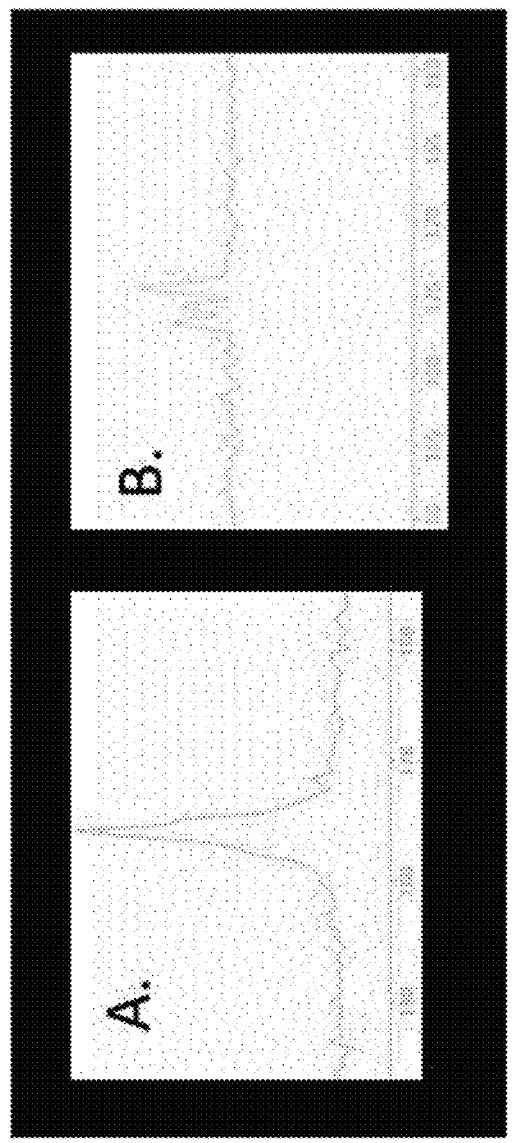
FIG. 7C is a comparison of averaged $^{13}$C CSI images illustrating the metabolism of hyperpolarized diethyl 1-$^{13}$C 2,3-d$_2$ succinate after intravenous injection in a RENCA tumor (left image) and in a breast tumor (right image) of two different mice.

A different biodistribution of the diethyl succinate is observed in the two types of tumors. FIG. 7A is a comparison of $^{13}$C FISP images illustrating the biodistribution of hyperpolarized diethyl 1-$^{13}$C 2,3-d$_2$ succinate after intravenous injection in a RENCA tumor (left image) and in a breast tumor (right image) of two different mice. FIG. 7B is a comparison of $^{13}$C CSI images illustrating the biodistribution of hyperpolarized diethyl 1-$^{13}$C 2,3-d$_2$ succinate after intravenous injection in a RENCA tumor (top image) and in a breast tumor (bottom image) of two different mice.

Figure 8A:
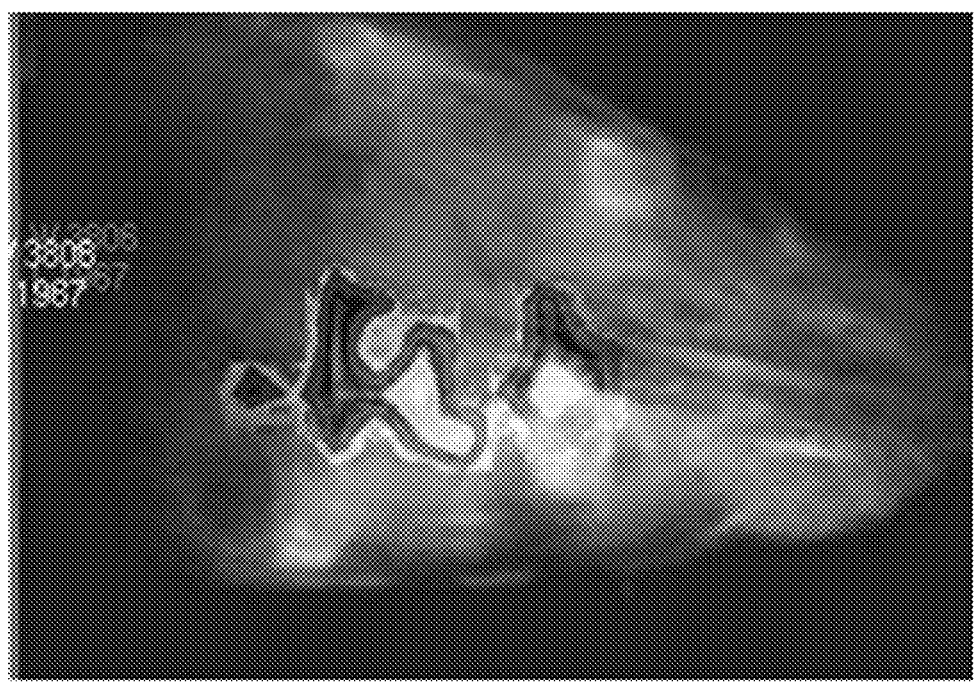
FIG. 8A is a $^{13}$C FISP image illustrating the biodistribution of 20 μmol of hyperpolarized diethyl 1-$^{13}$C 2,3-d$_2$ succinate delivered through carotid arterial injection in the head of a rat.
Figure 8B:
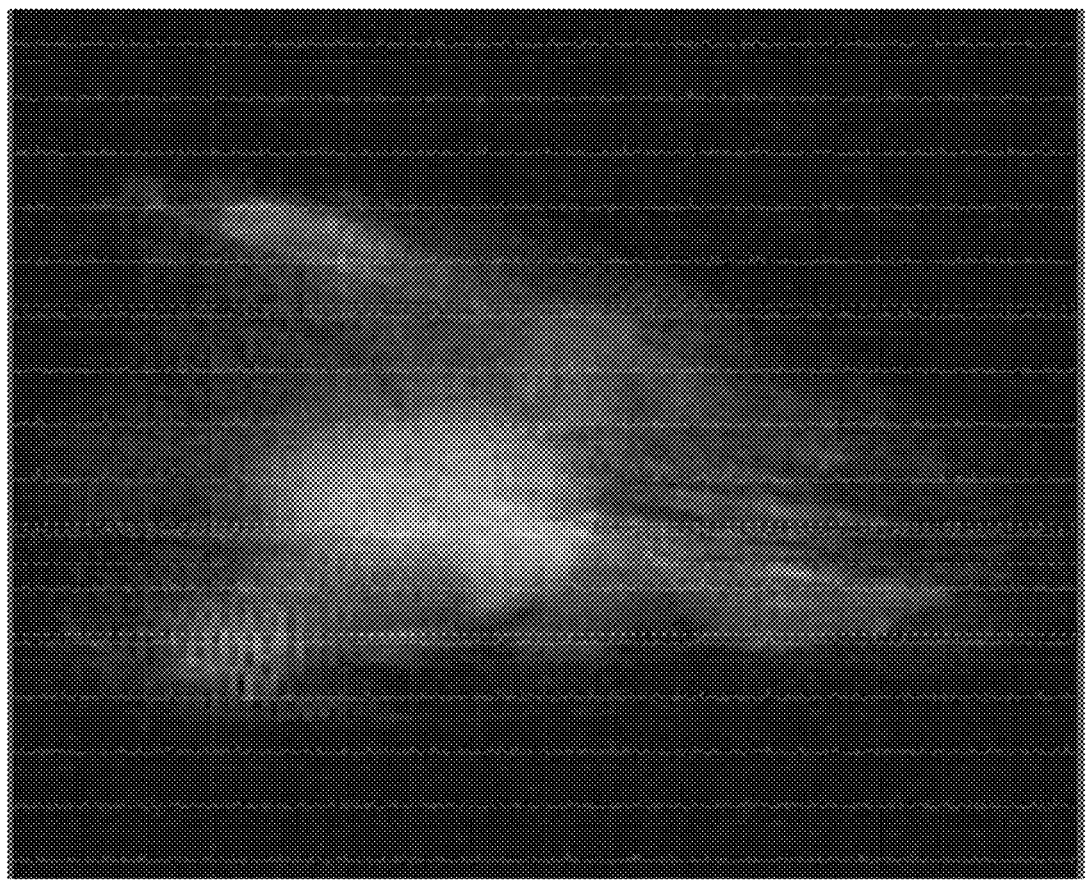
FIG. 8B is a $^{13}$C CSI spectrum illustrating the biodistribution of 20 μmol of hyperpolarized diethyl 1-$^{13}$C 2,3-d$_2$ succinate delivered through carotid arterial injection in the head of a rat.
Figure 8C:
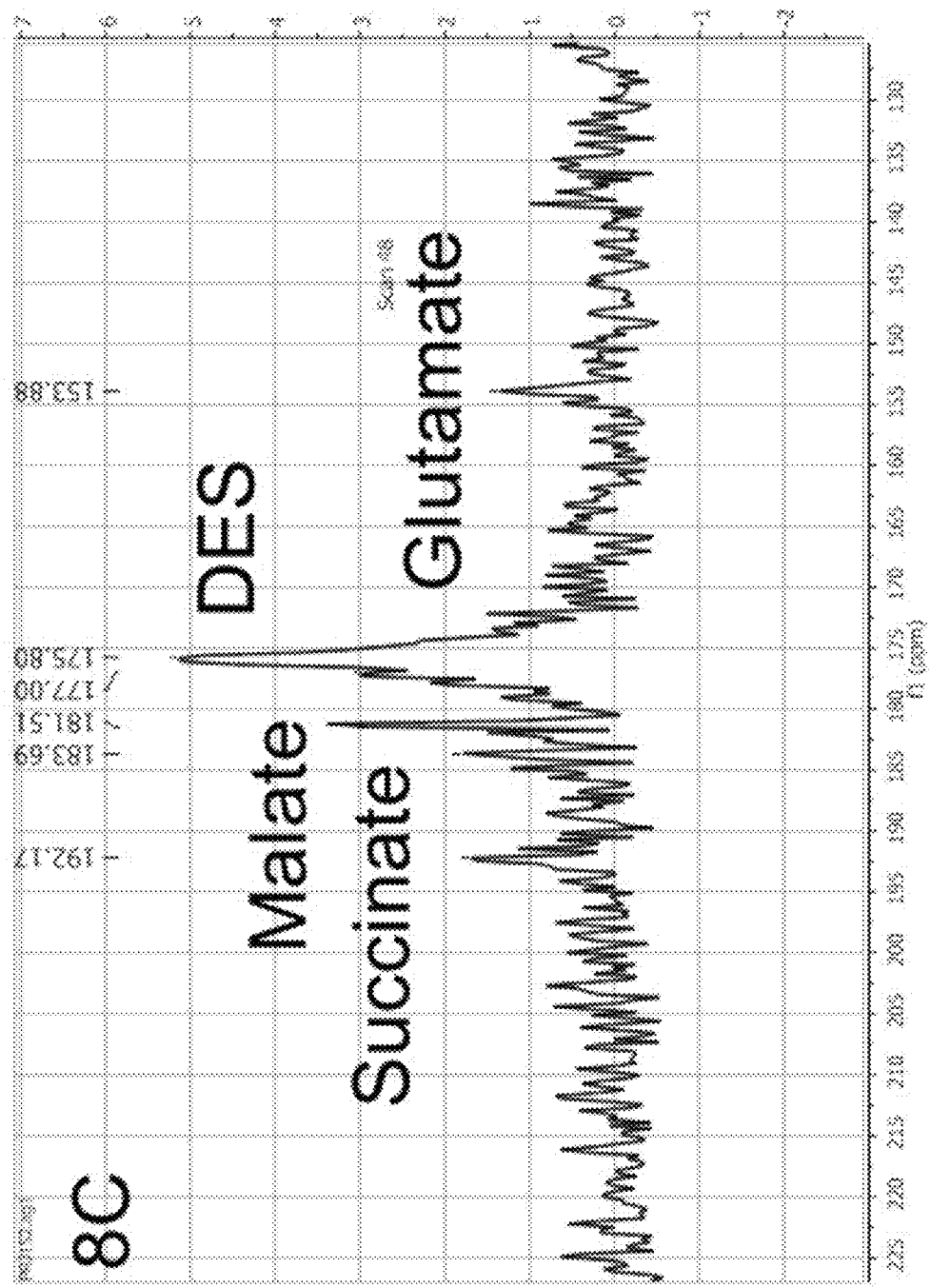
FIG. 8C illustrates a $^{13}$C MR spectrum of the head of a rat after carotid arterial injection of 20 μmol of hyperpolarized diethyl 1-$^{13}$C 2,3-d$_2$ succinate.

Metabolism of diethyl succinate is observed in both tumors using $^{13}$C CSI. Pulse and data acquisition was used with the volume coverage of 64 cm$^3$ to measure the flux rate of the compound using our dual tuned 4 cm ID solenoid volume coil. FIG. 8C is a comparison of averaged $^{13}$C CSI images illustrating the metabolism of hyperpolarized diethyl 1-$^{13}$C 2,3-d$_2$ succinate after intravenous injection in a RENCA tumor (left image) and in a breast tumor (right image) of two different mice.

Example 8

Imaging of TCA Cycle Metabolism in a Rat Brain by Hyperpolarization

Hyperpolarized diethyl succinate was used to detect metabolism in a rat brain as well as demonstrate that the compound crosses the blood-brain barrier. PHIP was used to hyperpolarize diethyl 1-$^{13}$C 2,3-d$_2$ succinate. The hyperpolarized solution was injected via the carotid artery of normal male Sprague Dawley rat (N=3) in near physiological concentrations (10-20 µmol). A $^1$H/$^{13}$C dual resonance 4 cm ID solenoid volume coil was utilized for $^{13}$C hyperpolarized in vivo imaging and spectroscopy. $^{13}$C FISP sequence with a flip angle of 60°, FOV 6 or 7 cm, and slice thickness of 15.2 mm was used to observe the biodistribution of the compound. $^{13}$C CSI with a 1 ms gauss pulse, 200 ms TR, 8×8 or 16×16 matrix, FOV ranging from 2.64 cm to 4 cm, slice thickness of 8 to 12 mm was used. CSI was processed using 3DiCSI software (Columbia University, Qui Zhao). The flux rate of the compound within the tumor was determined using a simple pulse and acquire $^{13}$C sequence. All $^{13}$C imaging and spectroscopy was done on a horizontal bore Bruker Avance 4.7T animal scanner.

Real time biodistribution of the hyperpolarized compound reveals that diethyl succinate is delivered to the brain of the rat by carotid arterial injection. FIG. 8A is a $^{13}$C FISP image illustrating the biodistribution of 20 µmol of hyperpolarized diethyl 1-$^{13}$C 2,3-d$_2$ succinate delivered through carotid arterial injection in the head of a rat. The hyperpolarized succinate signal from the inflowing blood allowed for $^{13}$C imaging and spectroscopy up to 1 minute after injection. The majority of the hyperpolarized signal within the brain of the animal is also observed with $^{13}$C CSI. FIG. 8B is a $^{13}$C CSI spectrum illustrating the biodistribution of 20 µmol of hyperpolarized diethyl 1-$^{13}$C 2,3-d$_2$ succinate delivered through carotid arterial injection in the head of a rat.

TCA cycle metabolites are observed within 5 s of administration. $^{13}$C MR spectroscopy of the brain localized by the coil shows the formation of multiple downstream TCA cycle metabolic products from the injection of the hyperpolarized diethylsuccinate identified as succinate, malate, and glutamate. FIG. 8C illustrates a $^{13}$C MR spectrum of the head of a rat after carotid arterial injection of 20 µmol of hyperpolarized diethyl 1-$^{13}$C 2,3-d$_2$ succinate.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When "only A or B but not both" is intended, then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." Finally, where the term "about" is used in conjunction with a number, it is intended to include ±10% of the number. For example, "about 10" may mean from 9 to 11.

As stated above, while the present application has been illustrated by the description of embodiments, and while the embodiments have been described in considerable detail, it is not the intention to restrict or in any way limit the scope of the appended claims to such detail. Additional advantages and modifications will readily appear to those skilled in the art. Therefore, the application, in its broader aspects, is not limited to the specific details and illustrative examples shown. Departures may be made from such details and examples without departing from the spirit or scope of the general inventive concept.

The invention claimed is:

1. A method for determining a metabolic state of a patient, comprising:

detecting one or more hyperpolarized metabolic products of a hyperpolarized composition by magnetic resonance, the one or more hyperpolarized metabolic products formed by metabolism of the hyperpolarized composition in the patient or a tissue sample thereof, the hyperpolarized composition comprising at least one of a hyperpolarized dialkyl $^{13}$C succinate compound or a hyperpolarized dialkyl $^{13}$C fumarate compound; and determining the metabolic state of the patient according to the one or more hyperpolarized metabolic products detected by the magnetic resonance.

2. The method of claim 1, further comprising administering the hyperpolarized composition to the patient.

3. The method of claim 1, further comprising allowing at least a portion of the hyperpolarized composition to metabolize in the patient to form the one or more hyperpolarized metabolic products.

4. The method of claim 1, the hyperpolarized composition comprising at least one of:

the hyperpolarized dialkyl $^{13}$C succinate compound, represented by Formula I,

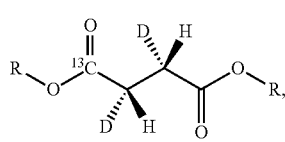

I or the hyperpolarized dialkyl $^{13}$C fumarate compound, represented by Formula II,

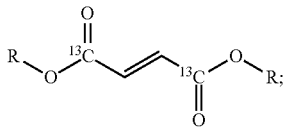

and each R independently being methyl, ethyl, n-propyl, 2-propyl, n-butyl, i-butyl, or t-butyl.

5. The method of claim 4, each R being ethyl.

6. The method of claim 1, the hyperpolarized composition comprising at least one of: hyperpolarized diethyl 1-$^{13}$C 2,3-$d_2$ succinate, hyperpolarized diethyl 1,4-$^{13}$C succinate, or hyperpolarized diethyl 1,4-$^{13}$C fumarate.

7. The method of claim 1, the one or more hyperpolarized metabolic products comprising at least one hyperpolarized metabolic product of the tricarboxylic acid (TCA) cycle.

8. The method of claim 1, further comprising:
obtaining data from the detecting of the one or more hyperpolarized metabolic products of the hyperpolarized composition by magnetic resonance; and
comparing the obtained data with preexisting data to determine a disease state in the patient.

9. The method of claim 8, the preexisting data corresponding to a baseline spectrum.

10. The method of claim 8, the disease state producing at least one of different metabolic products and/or different quantities of the same metabolic products from the patient's tricarboxylic acid (TCA) cycle compared to metabolic products from the patient's TCA cycle in the absence of the disease state.

11. The method of claim 8, the disease state comprising a cancer, the cancer being characterized by production of at least one of different metabolic products and/or different quantities of the same metabolic products from the patient's tricarboxylic acid (TCA) cycle compared to metabolic products from the patient's TCA cycle in the absence of the cancer.

12. The method of claim 8, the disease state comprising a neurodegenerative disease state comprising one or more of: Alzheimer's Disease, Parkinson's Disease, Huntington's Disease, or amyotrophic lateral sclerosis, the neurodegenerative disease state being characterized by production of at least one of different metabolic products and/or different quantities of the same metabolic products from the patient's tricarboxylic acid (TCA) cycle compared to metabolic products from the patient's TCA cycle in the absence of the neurodegenerative disease state.

13. The method of claim 8, the disease state comprising a heart disease, the heart disease state being characterized by production of at least one of different metabolic products and/or different quantities of the same metabolic products from the patient's tricarboxylic acid (TCA) cycle compared to metabolic products from the patient's TCA cycle in the absence of the heart disease state.

14. The method of claim 8,
the preexisting data corresponding to the patient's tricarboxylic acid (TCA) cycle metabolic products in the disease state; and
the detecting in the patient of the one or more hyperpolarized metabolic products of the hyperpolarized composition occurring after the patient has been subjected to a therapy.

15. The method of claim 8,
the preexisting data corresponding to the patient's tricarboxylic acid (TCA) cycle metabolic products in a cancerous state; and
the detecting in the patient of the one or more hyperpolarized metabolic products of the hyperpolarized composition occurring after the patient has been subjected to a chemotherapy.

16. A method for preparing one or more detectable hyperpolarized metabolic products in a patient or a tissue sample thereof, comprising:
administering to the patient or the tissue sample thereof a hyperpolarized composition, the hyperpolarized composition comprising at least one of a hyperpolarized dialkyl $^{13}$C succinate compound or a hyperpolarized dialkyl $^{13}$C fumarate compound; and allowing at least a portion of the hyperpolarized composition to metabolize in the patient or the tissue sample thereof to prepare the one or more detectable hyperpolarized metabolic products in the patient.

17. The method of claim 16, the hyperpolarized composition comprising at least one of:
the hyperpolarized dialkyl $^{13}$C succinate compound, represented by Formula I,

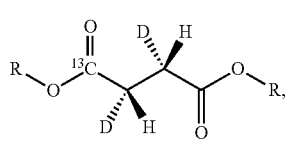

or the hyperpolarized dialkyl $^{13}$C fumarate compound, represented by Formula II,

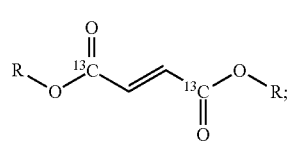

and each R independently being methyl, ethyl, n-propyl, 2-propyl, n-butyl, i-butyl, or t-butyl.

18. The method of claim 17, each R being ethyl.

19. The method of claim 16, the hyperpolarized composition comprising at least one of: hyperpolarized diethyl 1-$^{13}$C 2,3-$d_2$ succinate, hyperpolarized diethyl 1,4-$^{13}$C succinate, or hyperpolarized diethyl 1,4-$^{13}$C fumarate.

20. The method of claim 16, the one or more hyperpolarized metabolic products comprising at least one hyperpolarized metabolic product of the tricarboxylic acid (TCA) cycle.

21. The method of claim 16, the patient being subject to a disease state which produces at least one of different metabolic products and/or different quantities of the same metabolic products from the patient's tricarboxylic acid (TCA) cycle compared to metabolic products from the patient's TCA cycle in the absence of the disease state.

22. The method of claim 21, the disease state comprising a cancer, the cancer being characterized by production of at least one of different metabolic products and/or different quantities of the same metabolic products from the patient's tricarboxylic acid (TCA) cycle compared to metabolic products from the patient's TCA cycle in the absence of the cancer.

23. The method of claim 21, the disease state comprising a neurodegenerative disease state comprising one or more of: Alzheimer's Disease, Parkinson's Disease, Huntington's Disease, or amyotrophic lateral sclerosis, the neurodegenerative disease being characterized by production of at least one of different metabolic products and/or different quantities of the same metabolic products from the patient's tricarboxylic acid (TCA) cycle compared to metabolic products from the patient's TCA cycle in the absence of the neurodegenerative disease.

24. The method of claim 21, the disease state comprising a heart disease, the heart disease being characterized by production of at least one of different metabolic products and/or different quantities of the same metabolic products from the patient's tricarboxylic acid (TCA) cycle compared to metabolic products from the patient's TCA cycle in the absence of the heart disease.

25. The method of claim 1, the detecting by magnetic resonance comprising magnetic resonance imaging of the one or more hyperpolarized metabolic products of the hyperpolarized composition in the patient, the magnetic resonance imaging being effective to provide one or more images corresponding to the metabolic state of the patient.

26. The method of claim 1, the detecting by magnetic resonance comprising magnetic resonance spectroscopy of the one or more hyperpolarized metabolic products of the hyperpolarized composition in the patient or the tissue sample thereof, the magnetic resonance spectroscopy being effective to provide at least one spectrum corresponding to the metabolic state of the patient.

27. The method of claim 11, the cancer comprising one or more of: renal carcinoma, lymphoma, or breast cancer.

28. The method of claim 22, the cancer comprising one or more of: renal carcinoma, lymphoma, or breast cancer.

* * * * *